(12) United States Patent
Sauerer

(10) Patent No.: US 12,105,078 B2
(45) Date of Patent: Oct. 1, 2024

(54) DEMULSIFIER ANALYSIS FRAMEWORK

(71) Applicant: Schlumberger Technology Corporation, Sugar Land, TX (US)

(72) Inventor: Bastian Sauerer, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 10 days.

(21) Appl. No.: 18/184,708

(22) Filed: Mar. 16, 2023

(65) Prior Publication Data

US 2023/0296581 A1 Sep. 21, 2023

Related U.S. Application Data

(60) Provisional application No. 63/320,414, filed on Mar. 16, 2022.

(51) Int. Cl.
*G01N 33/24* (2006.01)
*G01N 33/18* (2006.01)

(52) U.S. Cl.
CPC ....... *G01N 33/246* (2013.01); *G01N 33/1833* (2013.01)

(58) Field of Classification Search
CPC ... G01N 21/95; G01N 33/1833; G01N 33/246
See application file for complete search history.

(56) References Cited

U.S. PATENT DOCUMENTS

| | | | |
|---|---|---|---|
| 10,968,402 B1 * | 4/2021 | Raynel | C10G 33/04 |
| 11,332,677 B2 * | 5/2022 | White | G01F 1/86 |
| 11,492,557 B2 * | 11/2022 | Lopez Andreu | C10G 31/08 |
| 2014/0360920 A1 | 12/2014 | Reyes Avila et al. | |
| 2017/0327753 A1 | 11/2017 | Kamble | |
| 2020/0200005 A1 | 6/2020 | Guo et al. | |
| 2021/0348069 A1 | 11/2021 | White et al. | |
| 2022/0035971 A1 | 2/2022 | Mahavadi et al. | |

OTHER PUBLICATIONS

Berger, P.D., "Designing and Selecting Demulsifiers for Optimum Field Performance on the Basis of Production Fluid Characteristics", SPE-16285-PA, SPE Production Engineering, 1988, 3(4), pp. 522-526.

(Continued)

*Primary Examiner* — An H Do
(74) *Attorney, Agent, or Firm* — Jeffrey D. Frantz

(57) ABSTRACT

A method can include receiving, by a demulsifier analysis framework, tensiometer data for an oil and water field sample that includes an added candidate demulsifier, where the tensiometer data include rheology data with respect to frequency and where the demulsifier analysis framework includes a model derived at least in part on bottle test data for demulsifiers in oil and water emulsions; determining a performance characteristic for the candidate demulsifier with respect to the oil and water field sample using the tensiometer data as input to the model of the demulsifier analysis framework without performing a bottle test on the oil and water field sample; and outputting, by the demulsifier analysis framework, the performance characteristic for the candidate demulsifier with respect to breaking an emulsion of the oil and water field sample.

17 Claims, 9 Drawing Sheets

(56) References Cited

OTHER PUBLICATIONS

Bourrel, M. et al., "The Relationship of Emulsion Stability to Phase Behavior and Interfacial Tension of Surfactant Systems", Journal of Colloid and Interface Science, 1979, 72(1), pp. 161-163.
Chen, D. et al., "Pilot Performance of Chemical Demulsifier on the Demulsification of Produced Water from Polymer/Surfactant Flooding in the Xinjiang Oilfield", Water, 2018, 10, 1874, pp. 1-9.
Chen, G. et al., "Study of Dynamic Interfacial Tension for Demulsification of Crude Oil Emulsions", SPE-65012, presented at the SPE International Symposium on Oilfield Chemistry, Houston, Texas, 2021, pp. 1-7.
Graciaa, A. et al., "Emulsion Stability and Phase Behavior for Ethoxylated Nonyl Phenol Sulfates", Journal of Colloid and Interface Science, 1982, 89(1), pp. 217-225.
Marquez, R. et al., "The Oscillatory Spinning Drop Technique. An Innovative Method to Measure Dilational Interfacial Rheological Properties of Brine-Crude Oil Systems in the Presence of Asphaltenes", Colloids Interfaces, 2021, 5, 42, 22 pages.
Poindexter, M. K. et al., "Applied Statistics: Crude Oil Emulsions and Demulsifiers", Journal of Dispersion Science and Technology, 2004, 25, pp. 311-320.
Rosano, H. L. et al., "Considerations on Formation and Stability of Oil/Water Dispersed Systems", Journal of the American Oil Chemists Society, 1982, 59, pp. 360-363.
Salager, J. L. et al, "Surfactant-Oil-Water Systems Near the Affinity Inversion, Part I: Relationship Between Equilibrium Phase Behavior and Emulsion Type and Stability", Journal of Dispersion Science Technology, 1982, pp. 279-292.
Search Report and Written Opinion of International Patent Application No. PCT/US2023/064540 dated Jun. 29, 2023, 8 pages.

\* cited by examiner

DEMULSIFIER ANALYSIS FRAMEWORK

RELATED APPLICATIONS

This application claims priority to and the benefit of a US Provisional Application having Ser. No. 63/320,414, filed Mar. 16, 2022, which is incorporated by reference herein in its entirety.

BACKGROUND

A demulsifier is a chemical that can be used to break emulsions such that emulsified phases can separate. An emulsion can be a dispersion of one immiscible liquid into another, which may be formed via one or more processes. For example, consider presence of one or more surface active agents (surfactants), physical mixing, temperature, pressure, etc., as one or more processes. An emulsion can be stable or unstable. A stable emulsion can include one or more chemicals such as one or more surfactants that reduce the interfacial tension (IFT) between two liquids to achieve stability. Stable emulsions can pose challenges in the oil and gas industry, particularly in processing where oil and water are to be separated.

A demulsifier can be applied in various situation such as, for example, in a separation process that can include one or more separators. For example, consider a multi-phase separator that can be a vessel that separates well fluid into at least two types of liquids, namely oil and water. The type of demulsifier selected can depend on the type of emulsion (e.g., oil-in-water or water-in-oil). Demulsifiers also find use in chemical analysis of oil and synthetic muds and to treat produced hydrocarbons. Demulsifiers can function due to one or more different functional groups (e.g., amines, polyhydric alcohols, sulphonates, polymer, etc.). Such functional groups can provide for a variety of different types of demulsifiers with different performance characteristics as to different types of emulsion breaking tasks.

As an example, a demulsifier can be applied in a process that helps to ensure that residual water and salt content in crude and oil content of separated water meet particular specifications. A demulsifier can disrupt the ordered structure of one or more natural surfactants that stabilize an emulsion, thereby enabling dispersed droplets to coalesce and form larger droplets that can move to an oil/water interface (e.g., oil above water due to buoyancy).

Cost-effective demulsifiers can be formulated for one or more applications, facilities, etc. A wide range of factors such as, for example, injection location, nature of oil and produced water, environmental demands, and equipment and facility limitations, can be evaluated in an effort to select or formulate a demulsifier and, for example, to minimize operational disruption and cost.

As explained, demulsifiers can perform various functions for various processes. In the context of water and oil emulsions, a demulsifier can facilitate separation of water and oil, which, in turn, can improve downstream processing.

SUMMARY

A method can include receiving, by a demulsifier analysis framework, tensiometer data for an oil and water field sample that includes an added candidate demulsifier, where the tensiometer data include rheology data with respect to frequency and where the demulsifier analysis framework includes a model derived at least in part on bottle test data for demulsifiers in oil and water emulsions; determining a performance characteristic for the candidate demulsifier with respect to the oil and water field sample using the tensiometer data as input to the model of the demulsifier analysis framework without performing a bottle test on the oil and water field sample; and outputting, by the demulsifier analysis framework, the performance characteristic for the candidate demulsifier with respect to breaking an emulsion of the oil and water field sample. A system can include a processor; memory operatively coupled to the processor; and processor-executable instructions stored in the memory to instruct the system to: receive tensiometer data for an oil and water field sample that includes an added candidate demulsifier, where the tensiometer data include rheology data with respect to frequency; determine a performance characteristic for the candidate demulsifier with respect to the oil and water field sample, without performance of a bottle test for the oil and water field sample, using the tensiometer data as input to a model derived at least in part on bottle test data for demulsifiers in oil and water emulsions; and output the performance characteristic for the candidate demulsifier with respect to the oil and water field sample. One or more computer-readable storage media can include processor-executable instructions to instruct a computing system to: receive tensiometer data for an oil and water field sample that includes an added candidate demulsifier, where the tensiometer data include rheology data with respect to frequency; determine a performance characteristic for the candidate demulsifier with respect to the oil and water field sample, without performance of a bottle test for the oil and water field sample, using the tensiometer data as input to a model derived at least in part on bottle test data for demulsifiers in oil and water emulsions; and output the performance characteristic for the candidate demulsifier with respect to the oil and water field sample. Various other methods, systems, etc., are also described herein.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
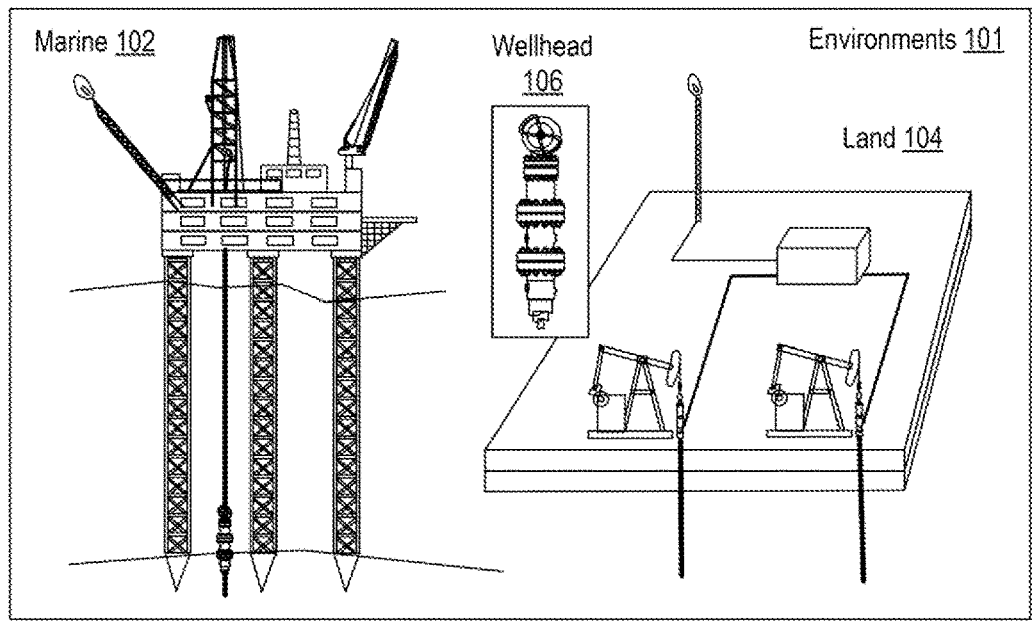
FIG. 1 is a series of diagrams of example environments and an example of a system.
Figure 1:
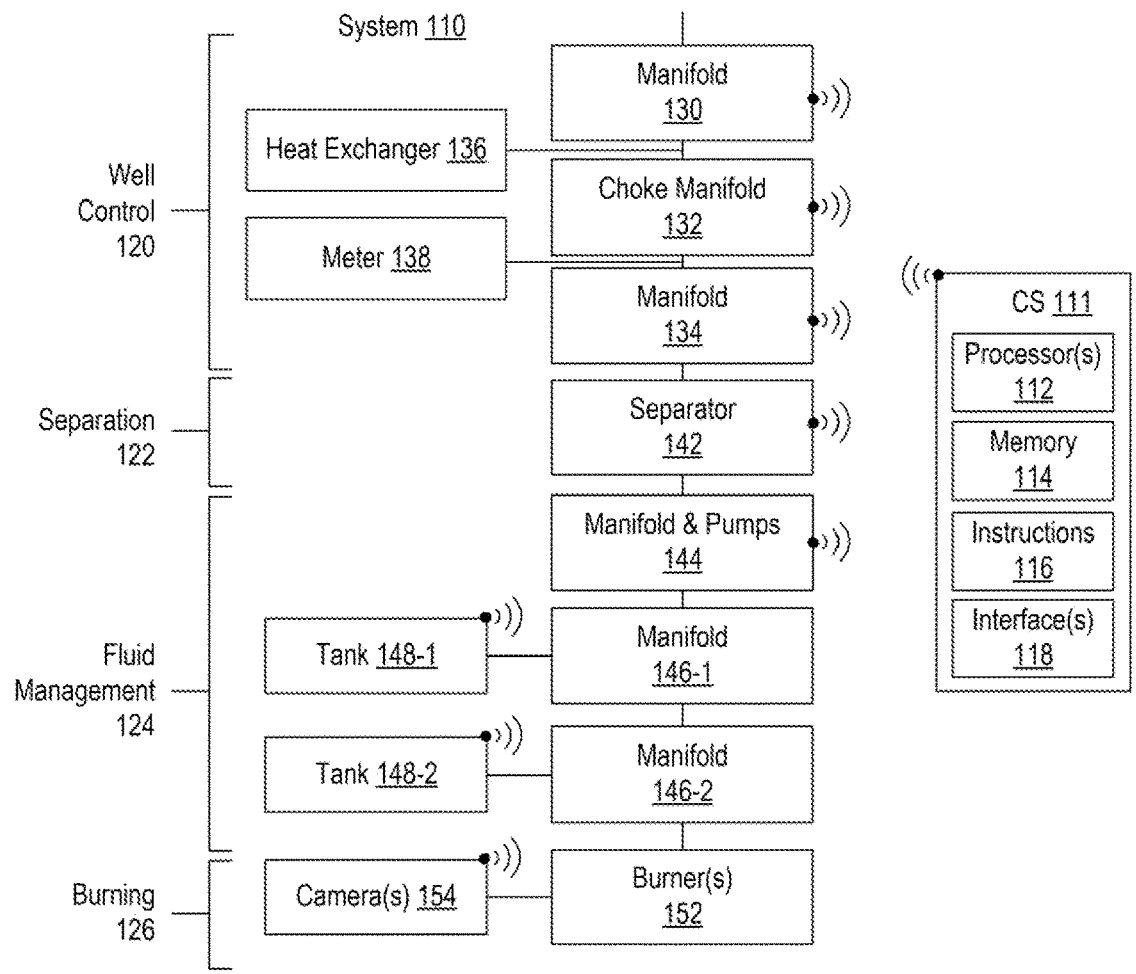

The following description is not to be taken in a limiting sense, but rather is made merely for the purpose of describing the general principles of the implementations. The scope of the described implementations should be ascertained with reference to the issued claims.

The selection and application of demulsifier chemicals for the oilfield commonly demands screening of a high number of chemicals as well as bottle testing of various blends of these chemicals to qualify a high performing product. A bottle test is a procedure in which different chemicals are added to bottle samples of an emulsion to determine which chemical is the most effective at breaking, or separating, the emulsion into oil and water. Once an effective chemical is determined, varying amounts of it can be added to bottle samples of the emulsion to determine the minimum amount required to break the emulsion effectively.

Bottle test results can be stated in terms of water separated from a sample with respect to time. For example, a sample can be placed in a tube and subject to test conditions, which can include temperature, shaking, etc. As an example, consider a protocol that calls for input of a certain amount of mechanical energy for a period of time to one or more standardized tubes filled with a predetermined amount of a sample, with or without demulsifier. A tube can include gradations (e.g., a scale) that allows for readings to be made as to a separated water phase. As time passes, an emulsion that is not stable will separate such that the amount of separated water increases with respect to time. In such an approach, a model may be used to characterize the breaking of the emulsion (e.g., a linear model, a nonlinear model, etc.). An effective demulsifier can break an emulsion more rapidly than natural processes, noting that a stable emulsion may remain stable for a considerable amount of time (e.g., hours, days, etc.). Through addition of different demulsifiers at different levels, an optimum or effective demulsifier can be identified. A demulsifier can be a mixture of components, which can include one or more solvents and one or more so-called intermediates, where an intermediate is a demulsifier. Table 1, below, shows some examples of bottle test data.

TABLE 1

Example bottle test results.

| No. | DM | Dose | 2 min | 4 min | 6 min | 8 min | Water | Oil | Int |
|---|---|---|---|---|---|---|---|---|---|
| 1 | None | 0 | — | — | — | — | — | Br | — |
| 2 | DM-A | 50 | 0.15 | 1.4 | 6 | 18 | C | B | B |
| 3 | DM-B | 50 | — | 0.05 | 0.3 | 1.5 | C | B | B |
| 4 | DM-C | 50 | — | — | 0.25 | 0.5 | C | Br | B |

In Table 1, the first column lists the bottle number, the second column lists the demulsifier tested or "none" if a sample is tested without a demulsifier, the third column lists the dose (e.g., in microliters, etc.), columns four to seven list the amount of free water at various times in appropriate volume units (e.g., milliliters), and columns eight to ten list subjective characteristics of a sample as to water, oil and interface, which include indicators such as "C" for clear, "B" for black or baggy, "Br" for brown, etc. As to such lists, water may include crystal clear, clear, hazy, oily water, oily glass, oil film on glass; oil may include black, brown, dark, light and visible water droplets; and interface may include sharp, fair, baggy, rags, loose and cone. As an example, additional data can include, for example, measured water drop after 1 hour and 90 minutes for longer retention times and/or Karl-Fischer (KF) titration, which provides an estimate of the remaining water content in an oil phase. For example, for DM-A in Table 1, a KF result was 1 percent; whereas, without a demulsifier, the KF result was 40 percent.

As to DM-A and DM-B, at 90 minutes, they both had free water values of 30, while DM-B had a KF result of 0.8 percent. Thus, depending on one or more factors that may be related to a field, DM-A and/or DM-B may be deemed effective where, if time is a concern, then DM-A may be selected over DM-B, and if the difference between 1 percent and 0.8 percent in the KF result is a concern, then DM-B may be selected. A selection process may also consider cost, handling, impact on equipment, downstream processing, environment, etc.

As an example, a bottle test can be performed at least in part in a subjective manner where subjective information is available, which may be handwritten information on a sheet of paper. As an example, results on a sheet of paper may be digitized where information can be extracted for storage in a database. Such information can include data and metadata. As an example, data for water drop out versus time may be extracted and presentable in a form of a plot (e.g., water drop out versus time), which may be represented as an image, a model (e.g., a rate model), etc. For example, consider generation of pixel image data for water drop out versus time where such pixel image data can be utilized for training one or more machine learning models (ML models) that can perform image analysis. As an example, generated images may include mixed images formed using bottle test data and other data such as tensiometer data where, for example, a ML model can receive tensiometer data and output corresponding bottle test data, which may be synthetic bottle test data based on training bottle test data. In such an approach, a framework may leverage ML models for images to characterize a candidate demulsifier or demulsifiers. Such an approach can be akin to training a ML model for plants where a plant can have an associated neighboring plant as in a plant ecosystem where training data can include images of the plant and associated neighboring plant and where a trained ML model can be provided an image of the plant alone to output a representation of an associated neighboring plant, which may be taken from a database and/or synthetically generated. As an example, various types of data can be represented in an image form, which may be images of plots (e.g., a bottle test data plot of water drop versus time, a tensiometer data plot of a property versus frequency, etc.).

As explained, a bottle test can include information for one or more demulsifiers (e.g., individual and/or formulations of multiple demulsifiers), which may be referred to as intermediates in a demulsifier solution with a solvent. Dosage or concentration can be varied. As indicated in Table 1, water drop out can be read from graduations on a bottle (e.g., a scale) and noted in two-minute intervals. Again, in Table 1, DM-A as in bottle number 2 performed well for a field sample from a Middle Eastern oil field, showing 18 ml of water dropping out after 8 minutes.

As an example, a framework can include features for digitizing bottle test data and/or for receiving digital files of bottle test data that may be entered via a graphical user interface (GUI). Such a framework can provide for organizing bottle test data, for example, with respect to field, type of oil, brine characteristics, dosage (e.g., concentration), time, and type of demulsifier or demulsifiers (e.g., in formulations). A framework can also provide for acquisition of tensiometer data and may provide for acquisition of field data, for example, as to separator performance. A database or databases can be generated with data sufficient to build one or more models that can utilize tensiometer data that can include rheology data for a candidate demulsifier (e.g., potential demulsifier) as input to generate one or more demulsifier performance characteristics of the candidate demulsifier as output. In such an example, the output can be generated without having to perform a bottle test on the candidate demulsifier, which, as explained, may take a considerable amount of time in setting up the bottle test and running the bottle test (e.g., consider setup and execution of a bottle test as in Table 1 as taking more than one hour). As an example, a framework can expedite candidate demulsifier performance characterization, which may be performed relatively rapidly using tensiometer data, which may be acquired using a tensiometer that generates digital data that can be automatically input to one or more models (e.g., without a user having to write information down on paper). A tensiometer may be provided with a field sample brine and a field sample crude oil where a demulsifier or demulsifiers are introduced and results generated upon pushing a button or other control.

Tensiometer data can be objective data that can be reproducible; whereas, as explained, bottle test data can include subjective data that may vary from person to person and may vary depending on a person's ability to read graduations on a bottle with respect to layers of fluids (e.g., phases, interface, etc.). Given a sufficiently large amount of bottle test data, outliers may be identified and optionally excluded and, for example, metrics may be generated as to quality and/or ranges (e.g., probabilities, statistics, etc.). As an example, a framework can receive tensiometer data that include rheology data and output one or more performance characteristics, optionally with one or more confidence intervals, etc. As to demulsifier efficiency as a performance characteristic, it may be defined as a volume of separated water divided by an initial volume of water in an emulsion of an oil and water field sample. As shown in Table 1, demulsifier efficiency can be assessed by observing volume of water dropping out of an emulsion; noting that original water content in an emulsion can vary. As an example, a performance characteristic for a demulsifier can be relative, for example, relative to a performance characteristic for one or more other demulsifiers. As an example, a framework can provide for ranking a candidate demulsifier, for example, with respect to one or more other demulsifiers, which may be other candidates and/or demulsifiers with corresponding data in a database upon which the framework is integrated or otherwise built upon.

As explained, the bottle test can be used to select an effective demulsifier (e.g., an efficient demulsifier). Following bottle test demulsifier screening to select a short-list of trial candidates, a final demulsifier selection can be made following field trials of the short-listed demulsifiers at a large scale in an actual field process scenario. Bottle tests while time-consuming play a role selecting the best demulsifier formulations to reduce the time and cost of field trials.

As an example, a demulsifier may be selected based in part on one or more residence times in a field process. For example, residence times can be determined for various flow rates for various pieces of fluid handling equipment. As an example, a residence time may be determined for a conduit that leads to a separator where the conduit may have an injection port for injection of demulsifier. As an example, an injection port location may be based on a residence time of a conduit and/or one or more other pieces of equipment and, for example, performance characteristics of one or more demulsifiers that can help to break a produced emulsion. As an example, a demulsifier analysis framework may include one or more features for assessing performance in a particular field. For example, consider a framework that can model fluid flow and/or separation such that a demulsifier can be selected that can be appropriately implemented in a particular field. In such an approach, one or more types of simulators may be included in the framework and/or operatively coupled to the framework. For example, consider the PIPESIM framework (SLB, Houston, Texas), which can perform fluid flow simulations for multiphase fluid and which can integrate with the DELFI environment (SLB, Houston, Texas).

The PIPESIM simulator includes solvers that can provide simulation results such as, for example, multiphase flow results (e.g., from a reservoir to a wellhead and beyond, etc.), flowline and surface facility performance, etc. The PIPESIM simulator may be integrated, for example, with the AVOCET production operations framework (SLB, Houston Texas). As an example, the PIPESIM simulator may be an optimizer that can optimize one or more operational scenarios at least in part via simulation of physical phenomena (e.g., consider separation and/or mixing of phases). The PIPESIM simulator can model various types of equipment such as chokes, safety valves, separators, and chemical injectors. The PIPESIM simulator has several options for modeling separators, including the following: separation defined with the rigorous PIPESIM simulator engine's flash calculations performed for various types of fluid definitions based on in situ pressure and temperature conditions; inline separators (downhole or surface) that discard liquid, gas, or water (e.g., using a specified separation efficiency); network separators that track both product and separated streams by adjusting for pressure continuity across separators to allow boundary-condition matching for each outlet stream; and separator configuration in series or parallel arrangements to model conditions for multistage separation trains. As an example, a demulsifier performance characteristic may be received by the PIPESIM simulator to simulate performance of one or more separation processes to generate simulation results where one or more control action can be taken in the field based on such results. In such an example, a demulsifier analysis framework can be operatively coupled to the PIPESIM simulator (e.g., a computational framework for performing simulations of field processes).

The DELFI environment or DELFI cognitive exploration and production (E&P) environment, is a secure, cognitive, cloud-based collaborative environment that integrates data and workflows with digital technologies, such as artificial intelligence and machine learning.

As an example, a scientific approach can be followed based on a model that demulsifier chemicals are surfactants, accumulating at and modifying the interface between the oil and water phases. Interfacial properties such as interfacial tension (IFT) and interfacial viscosity have been identified to play a crucial role for emulsion stability. See, e.g., Berger et al., "Designing and Selecting Demulsifiers for Optimum Field Performance on the Basis of Production Fluid Characteristics", SPE Production Engineering 1988, 522-526, hereinafter Berger. It has been noted that there is a common misconception in the role of IFT in regard to emulsion stability and that lowering IFT can benefit the stabilization of emulsions in some cases. See, e.g., Salager et al., "Surfactant-Oil-Water Systems Near the Affinity Inversion, Part I: Relationship Between Equilibrium Phase Behavior and Emulsion Type and Stability", J. Disp. Sci. Technol. 3, 1982, 279-92; Rosano et al., "Considerations on Formation and Stability of Oil/Water Dispersed Systems", JAOCS 59, 1982, 360-63; Graciaa et al., "Emulsion Stability and Phase Behavior for Ethoxylated Nonyl Phenol Sulfates", J. Colloid Interface Sci. 89, 1982, 217-25; and Bourrel et al., "The Relationship of Emulsion Stability to Phase Behavior and Interfacial Tension of Surfactant Systems", J. Colloid Interface Sci. 72, 1979, 161-63.

As an example, lowering the interfacial viscosity can be a possible mechanism by which demulsifiers break emulsions; noting that the relative solubility number, often used as a criterion in demulsifier assessment, actually shows no correlation to demulsifier performance as tested on 2400 field bottle tests. See Berger. In various instances, IFT lowering alone is not a reliable indicator for demulsification performance, as it can imply solely rapid migration to the oil/water interface, where mode of action depends on structure and other components present at the interface. Therefore, a scientific approach including a comprehensive multivariant analysis of various measurable interfacial properties and their correlation to actual demulsifier performance as inferred by bottle tests is required, which is currently unavailable in the open literature. See, e.g., Poindexter et al., "Applied Statistics: Crude Oil Emulsions and Demulsifiers", Journal of Dispersion Science and Technology 25, 2004, 311-320.

As an example, a demulsifier analysis framework can include a processor and memory that includes processor-executable instructions that can be executed to receive data for a demulsifier and analyze the data to determine efficiency of the demulsifier. In such an example, the framework can access a database, which can be created to provide correlation to an efficiency of one or more known demulsifier chemicals, as may be inferred from bottle testing to interfacial properties of an oil/water system. In such an example, data may include tensiometer data such as, for example, data from an oscillating pendant drop tensiometer. Such data can include various types of rheology data, for example, consider one or more types of moduli (e.g., viscous, elastic, viscoelastic, etc.).

As an example, a framework can provide for building and/or accessing a database. For example, consider a method that can correlate actual field efficiency of demulsifier intermediates and commercial products as inferred by standard bottle tests to interfacial property measurements. In such an example, the correlation of various interfacial properties at the oil/water interface, such as interfacial tension (IFT), viscoelastic modulus (E), elastic modulus (E'), and viscous modulus (E"), to results of standard bottle tests can provide for generation of a database that in turn facilitates the fast screening of new intermediates towards their demulsifier efficiency by the means of quick and easy interfacial property measurements. Such a method can include acquiring interfacial properties by means of a drop shape analyzer tensiometer that allows for the measurement of oscillating drops to infer viscoelastic properties of an oil drop in a bulk phase of an aqueous solution. An estimate of the demulsifier efficiency may be obtained, for example, from a regression model that correlates efficiency as measured in bottle tests to interfacial properties measured at the oil/water interface. In one embodiment, interfacial properties can be interfacial tension, viscoelastic modulus, elastic modulus, and viscous modulus, measured at the oil/water interface before and after the addition of a respective demulsifier chemical under analysis. In one or more other embodiments, one or more alternative interfacial or bulk properties may be used to estimate demulsifier efficiency.

As an example, a database may be utilized to train one or more machine learning models (ML models). For example, consider a trained ML model that can receive tensiometer data for a demulsifier (e.g., including IFT and one or more moduli) and that can output an efficiency for the demulsifier.

As an example, a framework may operate with or without a ML model. For example, a framework may operate using a database or using one or more ML models that may be trained using data of a database.

As an example, a sample of an emulsion and/or from an emulsion may be acquired in the field, for example, from a producing well or wells. In such an example, the sample may be transported to a facility that includes a tensiometer, which can be an instrument that is sensitive to external vibrations. As such, a tensiometer can be in a facility that is substantially isolated from external vibrations and/or mounted using one or more anti-vibration (e.g., vibration damping) mechanisms.

Various types of tensiometers are commercially available. For example, consider a pendant drop tensiometer that can be particularly applicable to relatively high interfacial tensions, though may measure down to approximately 1 mN/m. In a pendant drop tensiometer, a drop of the denser liquid is poised at the end of a syringe needle where the drop is of a sufficient size that its shape is deformed by gravity, but not so large that it detaches from the syringe. In such an approach, its shape can be determined by the balance of interfacial tension and gravity. The interfacial tension can be obtained from the drop shape and the densities of the two liquids. Such an approach can also be applied for a drop of the less-dense liquid by inverting the syringe. For example, consider a drop of a less dense phase being formed at the end of a syringe that faces upward in the direction of gravity in a surrounding denser phase. In such an example, buoyancy can cause a drop of the less dense phase to orient itself upwardly from the end of the syringe.

As an example, a tensiometer may include one or more oscillation mechanisms that can provide for imparting energy that can cause forces to impact a drop. In such an example, the drop can experience the forces can react, which can allow for acquisition of one or more rheologic properties. For example, consider a tensiometer that can impart oscillations for one or more frequencies where rheologic property data can be acquired. In such an example, plots can be generated of modulus versus frequency for components of an emulsion, which can include one or more demulsifiers that may be at one or more levels, ratios, etc.

As to viscoelastic properties, these can relate to interfacial rheology such as viscoelastic behavior and stress relaxation of an interface. As an example, rheology data can include viscous data, elastic data or viscous and elastic data. In a simple system of water and air, the IFT is constant and independent of changing area. However, if a surfactant is present, the physics can be quite complex. A surfactant can adsorb and form a layer at the interface. In equilibrium the molecules or particles occupy a certain amount of space at the interface and have a mean distance from each other. The resulting equilibrium interfacial concentration is characteristic of the system and depends on parameters like the participating phases, the interfacially active component and its bulk concentration. When the available interfacial area changes by changing the volume of a drop or by moving barriers across the interface the interfacially active components react to the deflection out of the equilibrium state.

When the interfacial area is decreased, the interfacial concentration increases, and the system tries to reach its equilibrium by desorbing the active components from the interface. When the interfacial area is increased, the interfacial concentration decreases and the equilibrium state is restored by adsorbing active components.

As the interfacial concentration of active components changes, the interfacial tension between the phases changes accordingly. For example, when the surfactant concentration at the interface increases by decreasing the available area, the interfacial tension will decrease as well. And, if the area is being increased, so does the interfacial tension. The reaction by the interfacially active components can occur at different speeds. This can depend on various factors such as, for example, the mobility of the components inside the bulk phase, the bulk concentration and the interfacial energy between the phases.

As an example, interfacial behavior can be described by the complex viscoelastic modulus E* (or E), which includes an elastic part E' and a viscous part E": $E^*=E'+iE"$. The complex viscoelastic modulus can be measured by continuously decreasing and increasing the interfacial area in an oscillatory manner. When the interfacial area is changed sinusoidally the interfacial tension also changes sinusoidally. The two sine waves are shifted by the phase shift. The phase shift depends on the reaction speed of the interfacially active components. The faster the interfacially active components react by adsorbing and desorbing to the interface the larger the phase shift becomes. The elastic modulus E' and the viscous modulus E" can be calculated from the sinusoidal area and tension change:

$$E'=\Delta\sigma(A_o/\Delta A)\cos \phi$$

$$E"=\Delta\sigma(A_o/\Delta A)\sin \phi$$

Above, $\Delta\sigma$ and $\Delta A$ are the peak-to-peak amplitudes of the interfacial tension and interfacial area, $A_o$ is the mean interfacial area and $\phi$ is the phase shift.

As explained, a tensiometer can include features that enable the measurement of the viscoelastic modulus. For example, with an optical contact angle goniometer and drop shape analysis system, oscillating pendant drops can be created. As an example, using a spinning drop video tensiometer, the rotational velocity of a spinning drop can be oscillated or using a dynamic contact angle measuring device and force tensiometer, the position of the barriers of a Langmuir through trough can be oscillated. Once the viscoelastic behavior has been optimized the influence on the stability or instability of an emulsion can be analyzed, for example, with a dispersion stability analysis system.

As explained, selection and application of demulsifier chemicals to ensure improved control of oil/water emulsions in oilfield operations tends to be a complex and tedious task. Numerous factors of chemical and physical nature have a direct impact on emulsion stability and therefore the separation processes. Demulsifier formulations often need to be selected specifically for each respective process system. Owing to the high number of interacting factors, representative testing and screening for suitable demulsifiers tends to follow a holistic approach, taking many variables into account. To date there is however no universal screening test other than the bottle test, which is in turn not standardized due to individual customization for specific oilfield situations. Hence, bottle tests are executed according to different procedures in different locations. Bottle tests demand various separate steps such as manual shaking of emulsions with various products in vials and the visual observation of multiple interfacial characteristics such as clarity of phases and smoothness of the interface and are therefore also highly subjective while requiring experienced experts. Replacing such a tedious practice with an automated and objective bulk or interfacial measurement allowing for rapidly screening multiple intermediates and formulations in regard to their potential demulsification efficiency is desirable in the industry.

Given that emulsion stability tends to be strongly defined by interfacial properties, which are physical quantities measurable using a tensiometer, a demulsifier analysis framework can be utilized for rapid screening of demulsifier chemical efficiency based on tensiometer interfacial measurements.

FIG. 1 shows examples of environments 101, including a marine environment 102 and a land environment 104 where the marine environment 102 includes various equipment and where the land environment 104 includes various equipment. As shown, each of the environments 101 can include one or more wellheads 106 (e.g., wellhead equipment). A wellhead can be a surface termination of a wellbore that can include a system of spools, valves and assorted adapters that, for example, can provide for pressure control of a production well. A wellhead may be at a land surface, a subsea surface (e.g., an ocean bottom, etc.), etc. As an example, conduits from multiple wellheads may be joined at one or more manifolds such that fluid from multiple wells can flow in a common conduit.

At various times, a well may be tested using a process referred to as well testing. During well testing, reservoir fluids can be produced at a separator at varying rates, for example, according to a predetermined schedule. Such tests may take less than two days to evaluate a single well or may take months to evaluate reservoir extent. Well testing can include one or more of a variety of well testing operations where tests may include, for example, one or more of buildup, drawdown, falloff, injection and interference. In various instances, fluid can flow from a well or wells to surface where the fluid is subjected to one or more well testing operations and generates scrap (e.g., waste fluid), which must be handled appropriately, for example, according to circumstances, regulations, etc. For example, consider loading waste fluid into a tanker for transport to a facility that can dispose of the waste fluid, handling waste fluid through combustion (e.g., flaring), etc.

As to the example environments 101 of FIG. 1, consider well testing as an operation that may be performed, for example, using equipment shown in the marine environment 102 and/or using equipment shown in the land environment 104. As an example, an environment may be under exploration, development, appraisal, etc., where such an environment includes at least one well where well fluid can be produced (e.g., via natural pressure, via fracturing, via artificial lift, via pumping, via flooding, etc.). In such an environment, various types of equipment may be on-site, which may be operatively coupled to well testing equipment.

FIG. 1 shows an example of a system 110 that can be operatively coupled to one or more conduits that can transport well fluid, for example, from one or more wellheads. As shown, the system 110 can include a computational system 111 (CS), which can include one or more processors 112, a memory 114 accessible to at least one of the one or more processors 112, instructions 116 that can be stored in the memory 114 and executable by at least one of the one or more processors 112, and one or more interfaces 118 (e.g., wired, wireless, etc.). In the example of FIG. 1, the system 110 is shown as including various communication symbols, which may be for transmission and/or reception of information (e.g., data, commands, etc.), for example, to and/or from the computational system 111. As an example, the computational system 111 can be a controller that can issue control instructions to one or more pieces of equipment in an environment such as, for example, the marine environment 102 and/or the land environment 104. As an example, the computational system 111 may be local, may be remote or may be distributed such that it is in part local and in part remote.

Referring again to the wellhead 106, it can include various types of wellhead equipment such as, for example, casing and tubing heads, a production tree, a blowout preventer, etc. Fluid produced from a well can be routed through the wellhead 106 and into the system 110, which can be configured with various features for well testing operations.

In the example of FIG. 1, the system 110 is shown to include various segments, which may be categorized operationally. For example, consider a well control segment 120, a separation segment 122, a fluid management segment 124, and a burning segment 126.

As shown in the example of FIG. 1, the well control segment 120 is an assembly of various components such as a manifold 130, a choke manifold 132, a manifold 134, a heat exchanger 136 and a meter 138; the separation segment 122 includes a separator 142; the fluid management segment 124 is an assembly of various components such as manifolds and pumps 144, a manifold 146-1, a manifold 146-2, a tank 148-1 and a tank 148-2; and the burning segment 126 includes a burner 152 and one or more cameras 154 (e.g., to observer burning, etc.).

As mentioned, in the example of FIG. 1, the system 110 includes various features for one or more aspects of well testing operations; noting that the system 110 may include lesser features, more features, alternative features, etc. For example, consider one or more of a gas specific gravity meter, a water-cut meter, a gas-to-oil ratio sensor, a carbon dioxide sensor, a hydrogen sulfide sensor, or a shrinkage measurement device. Various features may be upstream and/or downstream of a separator segment or a separator.

With respect to flow of fluid from a well or wells, such fluid may be received by the well control segment 120 and then routed via one or more conduits to the separation segment 122. In the example of FIG. 1, the well control segment 120 the heat exchanger 136 may be provided as a steam-heat exchanger and the meter 138 for measuring flow of fluid through the well control segment 120.

As mentioned, the well control segment 120 can convey fluid received from one or more wells to the separator 142. As an example, the separator 142 can be a horizontal separator or a vertical separator, and can be a two-phase separator (e.g., for separating gas and liquids) or a three-phase separator (e.g., for separating gas, oil, and water). A separator may include various features for facilitating separation of components of incoming fluid (e.g., diffusers, mist extractors, vanes, baffles, precipitators, etc.).

As an example, fluid can be single phase or multiphase fluid where "phase" refers to an immiscible component (e.g., consider two or more of oil, water, and gas).

As an example, the separator 142 can be used to substantially separate multiphase fluid into its oil, gas, and water phases, as appropriate and as present, where each phase emerging from the separator 142 may be referred to as a separated fluid. Such separated fluids may be routed away from the separator 142 to the fluid management segment 124. In various instances, the separated fluids may not be entirely homogenous. For example, separated gas exiting the separator 142 can include some residual amount of water or oil and separated water exiting the separator 142 can include some amount of oil or entrained gas. Similarly, separated oil leaving the separator 142 can include some amount of water or entrained gas.

As shown in the example of FIG. 1, the fluid management segment 124 includes flow control equipment, such as various manifolds and pumps (generally represented by the block 144) for receiving fluids from the separator 142 and conveying the fluids to other destinations, as well as additional manifolds 146-1 and 146-2 for routing fluid to and from fluid tanks 148-1 and 148-2. While two manifolds 146-1 and 146-2 and two tanks 148-1 and 148-2 are depicted in FIG. 1, it is noted that the number of manifolds and tanks can be varied. For instance, in one embodiment, the fluid management segment 124 can include a single manifold and a single tank, while in other embodiments, the fluid management segment 124 can include more than two manifolds and more than two tanks.

As to the manifolds and pumps 144, they can include a variety of manifolds and pumps, such as a gas manifold, an oil manifold, an oil transfer pump, a water manifold, and a water transfer pump. In at least some embodiments, the manifolds and pumps 144 can be used to route fluids received from the separator 142 to one or more of the fluid tanks 148-1 and 148-2 via one or more of the additional manifolds 146-1 and 146-2, and to route fluids between the tanks 148-1 and 148-2. As an example, the manifolds and pumps 144 can include features for routing fluids received from the separator 142 directly to the one or more burners 152 for burning gas and oil (e.g., bypassing the tanks 148-1 and 148-2) or for routing fluids from one or more of the tanks 148-1 and 148-2 to the one or more burners 152.

As noted above, components of the system 110 may vary between different applications (e.g., operations, etc.). As an example, equipment within each functional group of the system 110 may also vary. For example, the heat exchanger 136 could be provided as part of the separation segment 122, rather than of the well control segment 120.

In certain embodiments, the system 110 can be a surface well testing system that can be monitored and controlled remotely. Remote monitoring may be effectuated with sensors installed on various components. In some instances, a monitoring system (e.g., sensors, communication systems, and human-machine interfaces) can enable monitoring of one or more of the segments 120, 122, 124, and 126.

Figure 2:
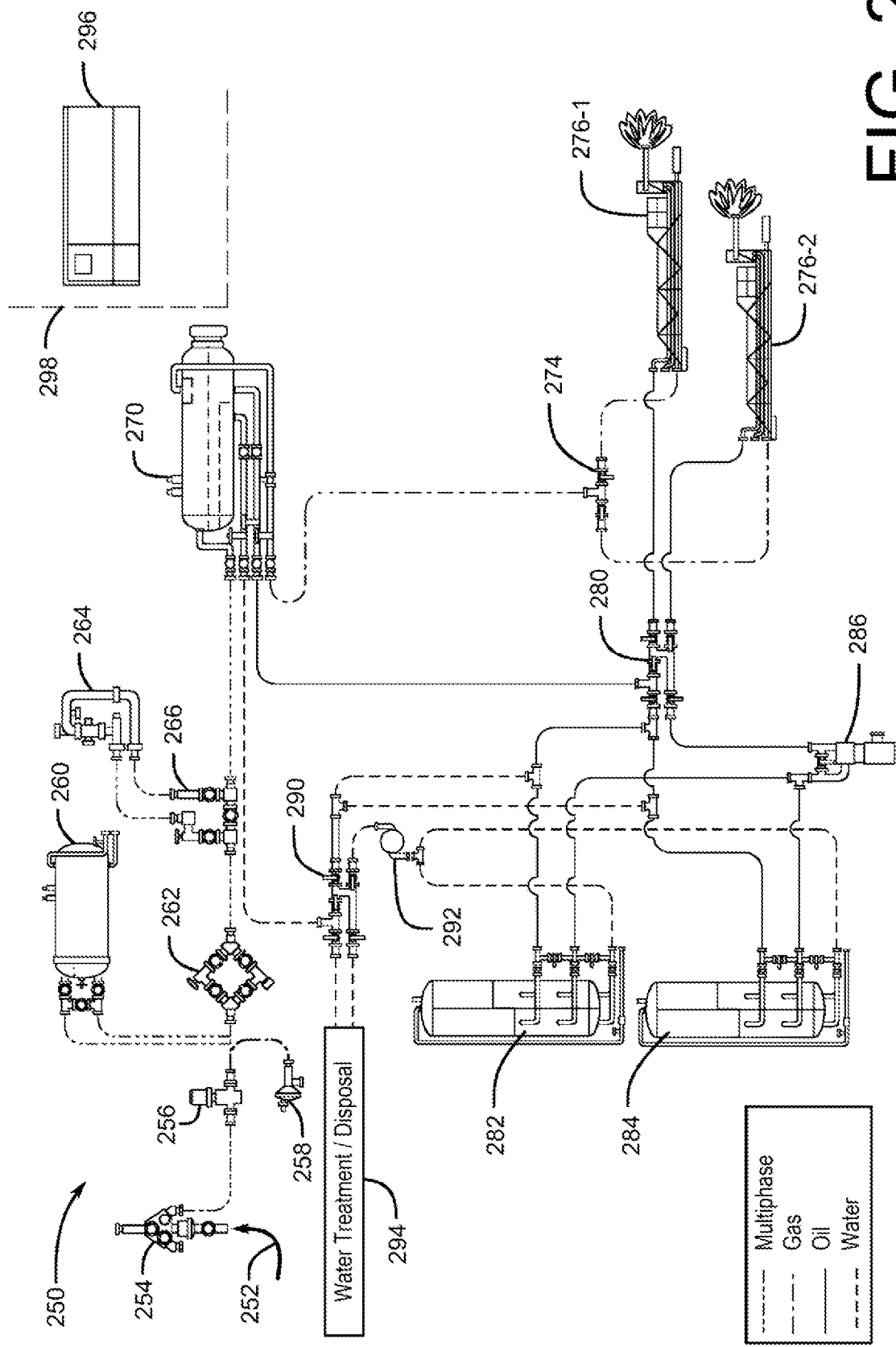
FIG. 2 is a diagram of an example of a system.

FIG. 2 shows an example of a system 250, which may be referred to as a surface well testing system. The system 250 can include various features of the system 110 of FIG. 1. Various equipment of the system 250, such as separation equipment, may be present at one or more types of sites (e.g., production sites, well testing sites, etc.).

In FIG. 2, a multiphase fluid (represented here by arrow 252) enters a flowhead 254 and is routed to a separator 270 through a surface safety valve 256, a steam-heat exchanger 260, a choke manifold 262, a flow meter 264, and an additional manifold 266. In the example of FIG. 2, the system 250 includes a chemical injection pump 258 for injecting chemicals into the multiphase fluid flowing toward the separator 270. For example, consider injection of one or more demulsifiers upstream the separator 270 and/or into the separator 270.

In the depicted embodiment of FIG. 2, the separator 270 is a three-phase separator that generally separates the multiphase fluid 252 into gas, oil, and water components. The separated gas is routed downstream from the separator 270 through a gas manifold 274 to either of the burners 276-1 and 276-2 for flaring gas and burning oil. The gas manifold 274 includes valves that can be actuated to control flow of gas from the gas manifold 274 to one or the other of the burners 276-1 and 276-2.

As shown, the separated oil from the separator 270 can be routed downstream to an oil manifold 280. Valves of the oil manifold 280 can be operated to permit flow of the oil to either of the burners 276-1 and 276-2 or either of the tanks 282 and 284. The tanks 282 and 284 can be of a suitable form but are depicted in FIG. 2 as vertical surge tanks each having two fluid compartments. This allows each tank to simultaneously hold different fluids, such as water in one compartment and oil in the other compartment. An oil transfer pump 286 may be operated to pump oil through the well testing system 250 downstream of the separator 270. The separated water from the separator 270 can be similarly routed to a water manifold 290. Like the oil manifold 280, the water manifold 290 includes valves that can be opened or closed to permit water to flow to either of the tanks 282 and 284 or to a water treatment and disposal apparatus 294. A water transfer pump 292 may be used to pump the water through the system.

In various instances, where an emulsion exists in produced fluid from a reservoir, one or more chemicals may be added to break the emulsion. For example, consider addition of one or more demulsifiers. The system 250 can operate more effectively when the separator 270 operates more effectively. For example, where an emulsion exists, separation by the separator 270 may be detrimentally impacted such that oil and water separation is not occurring efficiently (e.g., with respect to time, etc.). As explained, a demulsifier can be added to help make separation by the separator 270 more efficient, for example, such that more of the water (e.g., brine) in produced fluid can be removed from oil (e.g., crude oil) in the separator 270.

A well test area in which the well testing system 250 (or other embodiments of a well testing system) is installed may be classified as a hazardous area. In some embodiments, the well test area is classified as a Zone 1 hazardous area according to International Electrotechnical Commission (IEC) standard 60079-10-1:2015.

In the example of FIG. 2, a cabin 296 at a wellsite may include various types of equipment to acquire data from the well testing system 250. These acquired data may be used to monitor and control the well testing system 250. In at least some instances, the cabin 296 can be set apart from the well test area having the well testing system 250 in a non-hazardous area. This is represented by the dashed line 298 in FIG. 2, which generally serves as a demarcation between the hazardous area having the well testing system 250 and the non-hazardous area of the cabin 296.

The equipment of a system can be monitored during a process to verify proper operation and facilitate control of the process. Such monitoring can include taking numerous measurements, examples of which can include choke manifold temperature and pressures (upstream and downstream), heat exchanger temperature and pressure, separator temperature and pressures (static and differential), oil flow rate and volume from a separator, water flow rate and volume from a separator, and fluid levels in tanks of a system.

As an example, a mobile monitoring system may be provided. In such an example, monitoring of a process can be performed on a mobile device (e.g., a mobile device suitable for use in Zone 1 hazardous area, like the well test area). Various types of information may be automatically acquired by sensors and then presented to an operator via the mobile device. The mobile monitoring system may provide various functions, such as a sensor data display, video display, sensor or video information interpretation for quality-assurance and quality-control purposes, and a manual entry screen (e.g., for a digital tally book for recording measurements taken by the operator).

As an example, a site or a facility can include one or more computing devices. For example, consider a programmable logic controller (PLC), a gateway device, etc. As to a gateway device or simply gateway, it can include one or more features of an AGORA gateway (e.g., v.202, v.402, etc.) and/or another gateway. For example, consider an INTEL ATOM E3930 or E3950 Dual Core with DRAM and an eMMC and/or SSD. Such a gateway may include a trusted platform module (TPM), which can provide for secure and measured boot support (e.g., via hashes, etc.). A gateway may include one or more interfaces (e.g., Ethernet, RS485/422, RS232, etc.). As to power, a gateway may consume less than about 100 W (e.g., consider less than 10 W or less than 20 W). As an example, a gateway may include an operating system (e.g., consider LINUX DEBIAN LTS). As an example, a gateway may include a cellular interface (e.g., 4G LTE with Global Modem/GPS, etc.). As an example, a gateway may include a WIFI interface (e.g., 802.11 a/b/g/n). As an example, a gateway may be operable using AC 100-240 V, 50/60 Hz or 24 VDC. As to dimensions, consider a gateway that has a protective box with dimensions of approximately 10 in×8 in×4 in (e.g., 25 cm×20.3 cm×10.1 cm). A gateway may be operatively coupled to various pieces of equipment at a site and operatively coupled to one or more networks, which may include cloud resources (e.g., cloud platform resources). As an example, a gateway may be an edge-type of device that can be controlled, accessed, etc., remotely.

As an example, a method can provide for correlation of actual field efficiency of demulsifier intermediates and commercial products as inferred by standard bottle tests to interfacial property measurements. For example, various interfacial properties at the oil/water interface, such as interfacial tension (IFT), viscoelastic modulus (E), elastic modulus (E'), and viscous modulus (E"), can be correlated to results of standard bottle tests for generation of a database that facilitates rapid screening of existing and/or new intermediates towards their demulsifier efficiency. As explained, a demulsifier analysis framework can receive input as to interfacial property measurements and can generate output as to demulsifier performance (e.g., demulsifier efficiency).

As an example, a method can include acquiring interfacial properties using a drop shape tensiometer that allows for measurement of oscillating drops to infer viscoelastic properties of an oil drop in a bulk phase of an aqueous solution. As an example, such a method can estimate demulsifier efficiency, for example, from a regression model that correlates the efficiency as measured in bottle tests to interfacial properties measured at the oil/water interface. In an embodiment, the interfacial properties can include interfacial tension, viscoelastic modulus, elastic modulus, and viscous modulus, measured at the oil/water interface before and after the addition of a respective demulsifier chemical. In various embodiments, one or more alternative and/or additional interfacial and/or bulk properties may be used to estimate demulsifier efficiency.

As mentioned, various types of tensiometers exist. For example, consider oscillating spinning drop tensiometers (see, e.g., Marquez et al., "The Oscillatory Spinning Drop Technique. An Innovative Method to Measure Dilational Interfacial Rheological Properties of Crude Oil-Brine Systems in the Presence of Asphaltenes", Colloids Interfaces 5, 42, 2021, 1-22) and drop volume tensiometers (see, e.g., Gong et al., "Study of Dynamic Interfacial Tension for Demulsification of Crude Oil Emulsions", SPE International Symposium on Oilfield Chemistry, Houston, Texas, February 2001). In various examples, data from a pendent drop tensiometer with capability of drop oscillation allowing for optical drop shape analysis are utilized (see, e.g., Chen et al., "Pilot Performance of Chemical Demulsifier on the Demulsification of Produced Water from Polymer/Surfactant Flooding in the Xinjiang Oilfield", Water 10, 1874, 2018, 1-9). As an example, a system can include a pendent drop tensiometer. A pendent drop tensiometer can provide for accurate and sensitive measurement of interfacial tension in addition to rheological properties of oil/water interfaces.

Figure 3:
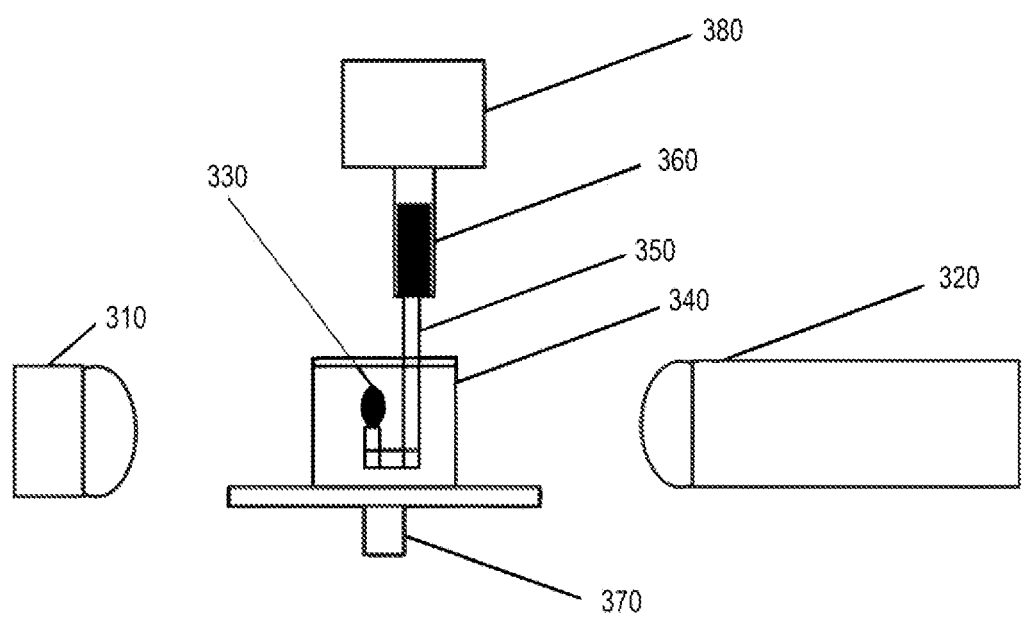
FIG. 3 is a diagram of an example of a system.

FIG. 3 shows an example of a system 300 that can generate tensiometer data. In the example of FIG. 3, the system 300 includes a light source 310, an optical camera 320, a drop shaped liquid 330 rising in a cuvette 340 from a U-shaped needle 350 as fluidly coupled to a syringe 360 where the cuvette 340 can be supported on an adjustable table 370 and where an oscillator 380 can control oscillations.

The system 300 can generate interfacial property data from drop shape imagery that can be in a digital form or digitized. For example, the cuvette 340 can be transparent such that light from the light source 310 can pass through liquid in the cuvette 340 whereby a shape or shapes of the drop 330 can be captured by the optical camera 320. As shown in the example of FIG. 3, the drop 330 can be a rising droplet due to buoyancy where the drop 330 includes liquid of a lighter phase (e.g., an oil phase composed of crude oil) as surrounded by a bulk, denser phase (e.g., an aqueous phase composed of brine). As an example, to help mitigate needle creeping effects, the U-shaped needle 350 can be a polymeric coated needle (e.g., consider polytetrafluoroethylene (PTFE), etc. The U-shaped needle 350 can be utilized to inject a lighter phase from the syringe 360. As an example, the height of the injection assembly can be adjusted relative to an optical path of the light 310 and optical camera 320 via the adjustable table 370, which can help to ensure proper capture of drop shape. As to oscillation of the drop 330 for purposes of measurements of rheologic properties this can be achieved by increasing and decreasing drop volume via control of the syringe 360. For example, the oscillator 380 can include one or more piezo elements to impart vibrations at one or more frequencies.

As an example, the system 300 can include one or more interfaces for control commands and/or data transmission. For example, consider an interface for control and/or data transmission of one or more of the oscillator 380, the adjustable table 370, the syringe 360, the light source 310 and the optical camera 320. The system 300 can include one or more processors and memory accessible to at least one of the one or more processors where the memory can store processor-executable instructions. As an example, the system 300 can include one or more databases and/or be operatively coupled to one or more databases and/or include one or more ML models and/or be operatively coupled to one or more ML models. As an example, the system 300 can be a demulsifier analysis framework system that can output demulsifier performance data (e.g., demulsifier efficiency) responsive to generation of interfacial property data, which can include rheological property data (e.g., viscoelastic data, etc.).

As an example, a method can include generating a drop using a crude oil phase and acquiring measurements with and without demulsifier present to infer a difference in measured interfacial properties. Such a method can include comparing a fluid system (e.g., phases) with and without demulsifier for one or more specific oils from a target oilfield. As an example, one or more transparent model oils may be utilized to serve as a bulk phase while a pendant drop of a heavier aqueous phase may be injected via a needle, for example, from a top position. As explained, a tensiometer may operate in a top drop manner where a dense phase is introduced into a lighter phase from a top position or in an inverse manner where a lighter phase is introduced into a denser phase (e.g., heavier phase) from a bottom position. In the top drop manner, a drop can extend downwardly under the influence of gravity while in a bottom drop manner, a drop can extend upwardly under the influence of gravity due to buoyancy.

As an example, a tensiometer can include one or more features of a KrÜss Scientific tensiometer, for example, consider a drop shape analyzer tensiometer having model designation DSA30R, which can generate IFT and rheology data, with a range of 0.01 to 2000 mN/m, a resolution of 0.01 mN/m, a precision of 0.2 mN/m and utilize one or more models (e.g., Young-Laplace) and make static and/or dynamic measurements. As to oscillating drop measurements, consider data for one or more of E, E', E", and phase shift, where oscillations may be performed according to one or more waveforms (e.g., sine wave) and where one or more models may be utilized (e.g., Lucassen-van den Tempel diffusional adsorption model).

As to the Young-Laplace model, it can be used for determining contact angle in drop shape analysis. For example, a drop shape can be analyzed based on the shape of an ideal sessile drop, the surface curvature of which results only from the force equilibrium between surface tension and weight. According to the Young-Laplace model, with a curved liquid surface, there is a relationship between the radii of curvature $r_1$ and $r_2$, the surface tension a and the Laplace pressure p:

$$\Delta p = \sigma(r_1^{-1} + r_2^{-1})$$

The Young-Laplace model can be used to determine surface tension of a liquid or the interfacial tension of a two-phase system using a pendant drop and for interfacial tension measurements with a spinning drop tensiometer.

As to the Lucassen-van den Tempel diffusional adsorption model, it may be utilized for frequency related data as there is a frequency dependence of the real and imaginary part of the dilational elasticity modulus that may be determined for various concentrations of demulsifier (e.g., 0 and greater). The real part of the modulus tends to increase with drop area oscillation frequency (v) and can be described by fitting the Lucassen-van den Tempel (LvdT) diffusional adsorption model:

$$E = E_0(1 + \xi + i\xi)/(1 + 2\xi + 2\xi^2), \xi = (v_D/2v)^{0.5}$$

where $E_0$ is the Gibbs elasticity and $v_D$ is the characteristic frequency of the diffusion transport mechanism, which can be determined by using acquired data and an appropriate fitting technique; noting E=E'+iE".

Figure 4:
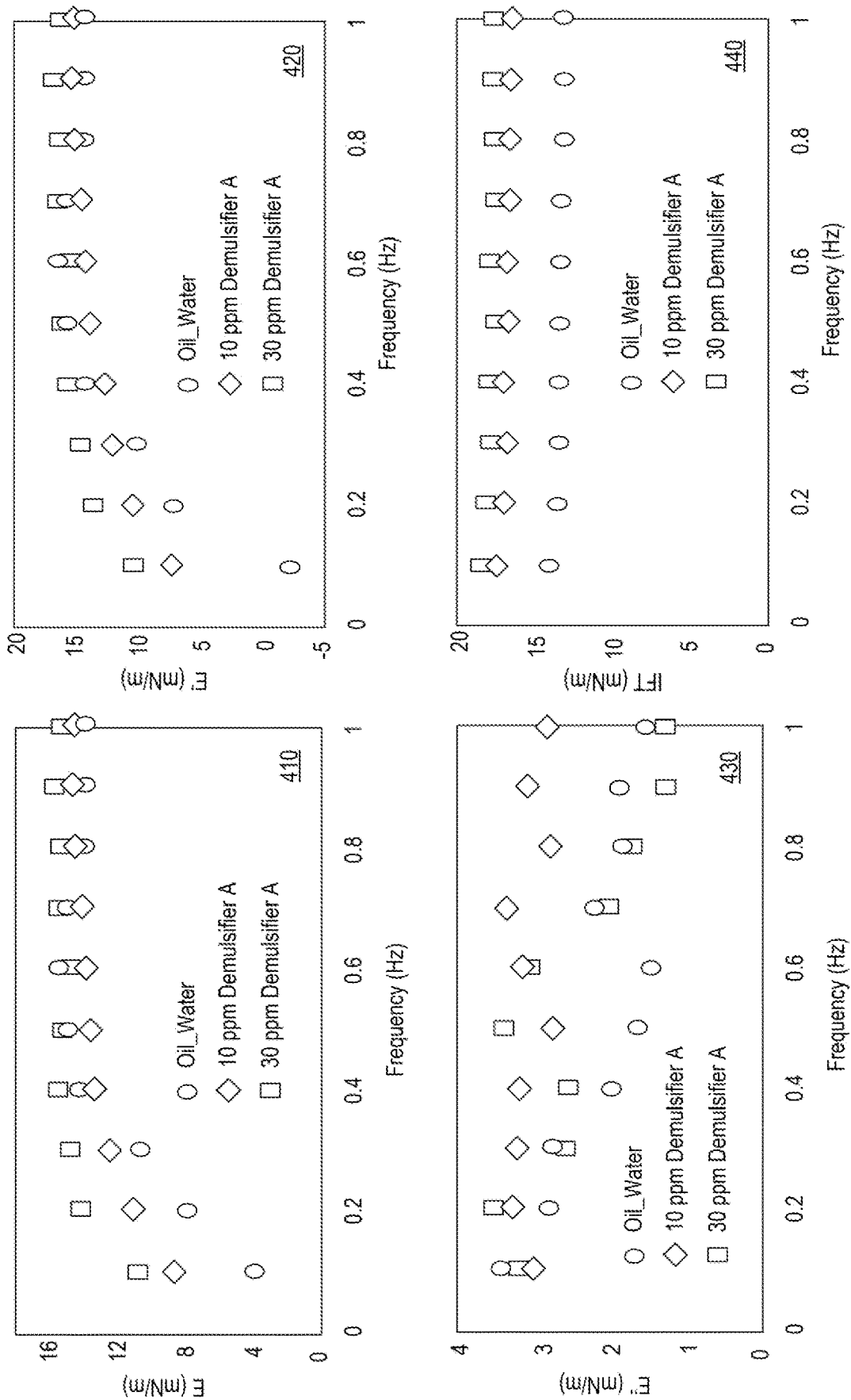
FIG. 4 is a series of diagrams of example plots of tensiometer data.

FIG. 4 shows example plots 410, 420, 430 and 440 of data from a tensiometer, which includes rheological data. As shown, the plot 410 shows data for E, the viscoelastic modulus (mN/m), versus frequency (Hz) for an oil and water system without a demulsifier, the oil and water system with 10 ppm of a demulsifier labeled demulsifier A, and with 30 ppm of the demulsifier labeled demulsifier A, while the plot 420 shows data for E', the viscous modulus (mN/m), versus frequency (Hz) and the plot 430 shows data for E", the elastic modulus (mN/m), versus frequency (Hz). In FIG. 4, the plot 440 shows data for IFT (mN/m) versus frequency (Hz).

As explained, results of interfacial tension and interfacial rheology measurements can be correlated to demulsifier efficiency as inferred from bottle tests. For example, consider performing one or more correlations via one or more of linear regression models, non-linear regression models, ML models and one or more other types of artificial intelligence algorithms.

Once correlations are revealed through statistical and/or probabilistical analysis of a database populated from measurements, new interfacial measurements on one or more demulsifier intermediates (e.g., new demulsifier intermediates) can be generated that allow for rapid screening and assessment of these chemistries regarding their potential for efficient demulsification.

Figure 5:
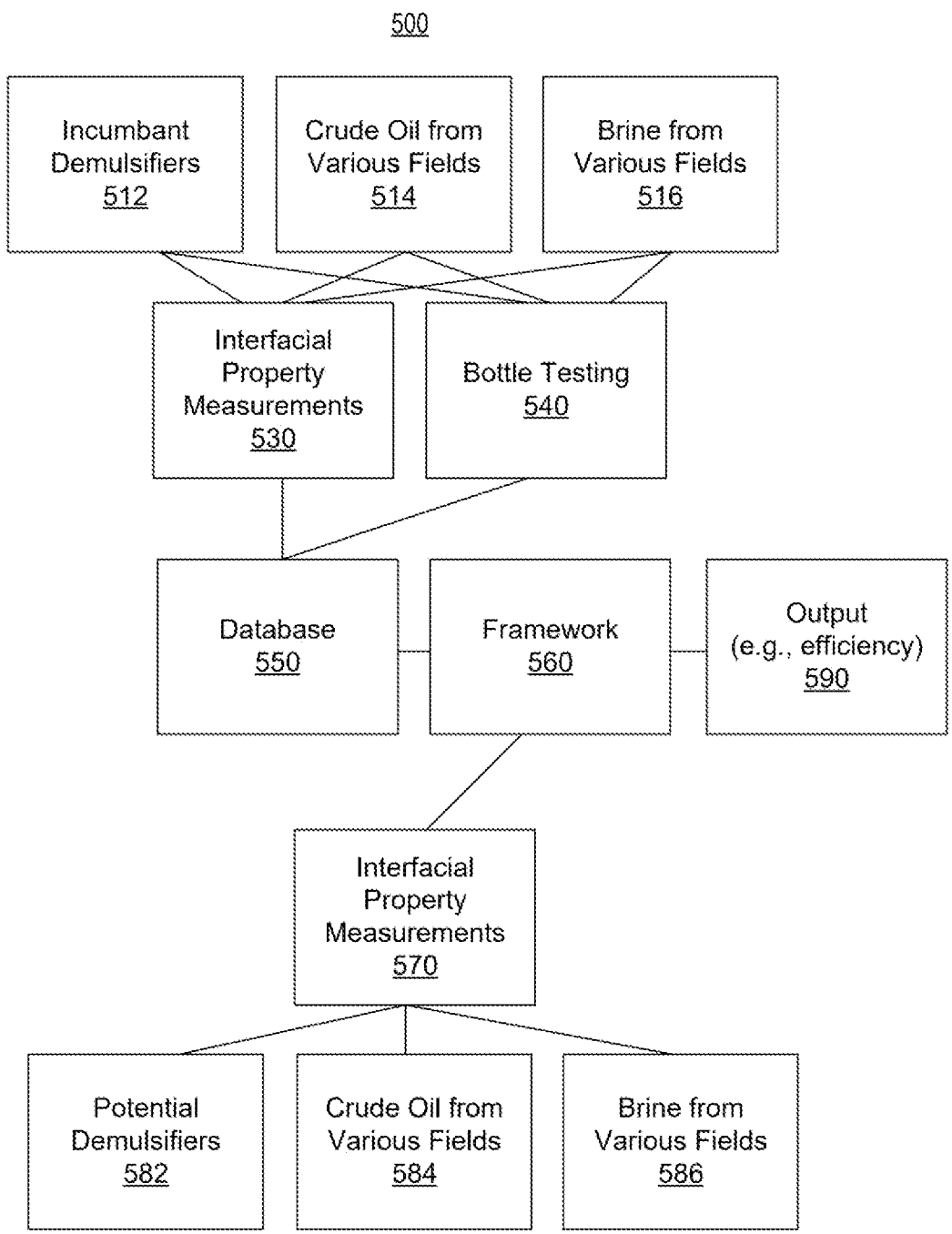
FIG. 5 is a diagram of an example of a system.

FIG. 5 shows an example of a workflow 500 that can generate a database 550 for a framework 560 where the framework 560 can be utilized to output demulsifier performance indicators 590 responsive to receipt of interfacial property measurements 570 for a one or more potential demulsifiers 582 (e.g., candidate demulsifiers), crude oil from various fields 584 and brine from various fields 586. As shown, the database 550 can be built from interfacial property measurements 530 and bottle testing 540 for incumbent demulsifiers 512, crude oil from various fields 514 and brine from various fields 516. As explained, interfacial property measurements can be generated using one or more tensiometers, where such measurements can include rheological property measurements (e.g., E, E', E", etc.).

As an example, the framework 560 can be a dynamic framework that can respond to receipt of data such as the interfacial property measurements 570 to generate output such as the output 590. Such a framework can reduce demand for bottle tests. For example, the output 590 can be generated for one or more of the potential demulsifiers 582 without performing a bottle test for the one or more of the potential demulsifiers 582. Such a framework can be robust and rapid as tensiometer measurements may be acquired more rapidly than bottle test results.

As an example, a laboratory or other facility may include one or more tensiometers that are operatively coupled to a framework, locally and/or remotely. As an example, a framework may be dynamically updated responsive to one or more database updates. For example, as additional bottle tests are performed, a database can be updated and one or more models, etc., can also be updated.

As an example, a field may be supplied with a stock of one or more candidate demulsifiers where one or more samples from the field can be transported to a facility to perform interfacial property measurements. In such an example, a framework can analyze the interfacial property measurements based on data included in a database to generate output as to performance of the one or more candidate demulsifiers. In such an example, one or more commands may be transmitted to the field to control selection of one of the one or more candidate demulsifiers and, for example, injection thereof into a process stream for emulsion breaking. Such an approach can include maintaining sensor data as to levels of candidate demulsifiers, performance of a separator, etc. For example, if a top ranked candidate demulsifier is at a low level in the field, a second ranked candidate demulsifier with a higher level in the field may be selected for injection, optionally where a request is issued to acquire an additional supply of the top ranked candidate demulsifier.

As explained, a rate determining step may be in transport of field samples to a facility that includes a tensiometer. As explained, by reducing demand for performing one or more bottle tests, an analysis of one or more candidate demulsifiers can be expedited. Such an approach, through use of a demulsifier analysis framework, can improve separation in the field as performance data for a candidate demulsifier can be generated more rapidly.

As explained, a framework can allow for rapid analysis as to variations of one or more properties such as the applicability of a specific intermediate in different regions by running a sweep to oils from various reservoirs, and to optimize a final blend by faster concentration screenings.

Figure 6:
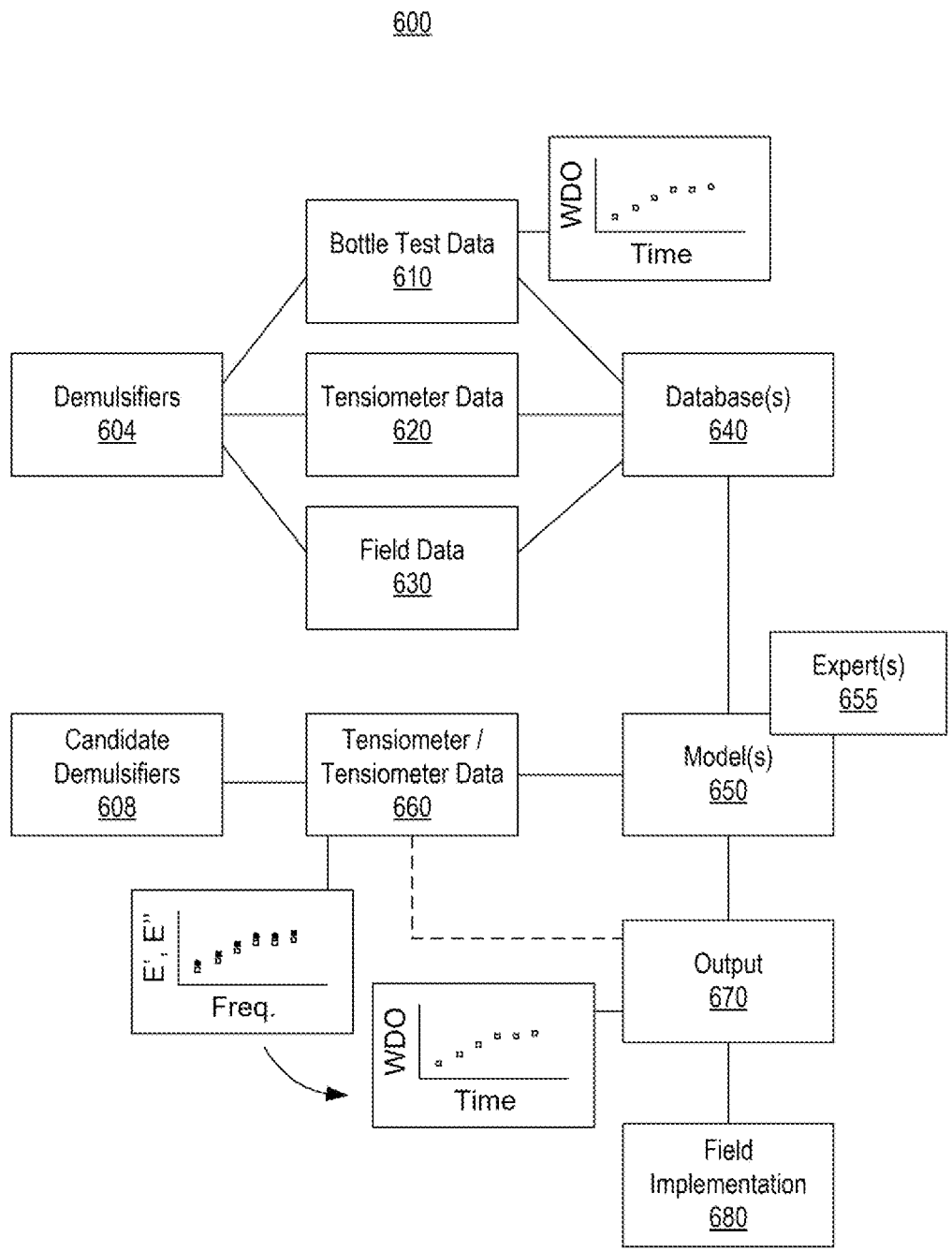
FIG. 6 is a diagram of example workflows.

FIG. 6 shows example workflows 600 where demulsifiers 604 are subjected to bottle testing to generate bottle test data 610, which can include time series data (e.g., water drop out (WDO) versus time), subjected to tensiometer measurements to generate associated tensiometer data 620, which can include time series and/or frequency series data (e.g., E, E', E" and/or IFT with respect to frequency), and subjected to field implementation to generate field data 630, which can include time series data (e.g., from one or more field transients, etc.), where the bottle test data 610, the tensiometer data 620 and the field data 630 can be stored in one or more databases 640. Such a workflow can be a database generation workflow.

FIG. 6 also shows model generation for one or more models 650, which can leverage data in the one or more databases 640, optionally with input from one or more experts 655, which may provide for supervised learning and/or semi-supervised learning and/or one or more functions, which may relate to unsupervised learning (e.g., consider hyperparameter tuning, etc.). As shown, candidate demulsifiers 608 can be subjected to tensiometer measurement techniques using one or more tensiometers to generate tensiometer data 660 for the candidate demulsifiers 608. For example, consider input that includes data such as data in one or more of the plots 410 (E), 420 (E'), 430 (E") and 440 (IFT) of FIG. 4. As explained, tensiometer data can include data with and without demulsifier, data with respect to frequency, data with respect to time, etc. The tensiometer data 660 can be utilized directly and/or indirectly as input to at least one of the one or more models 650 to generate output 670, which may be then utilized for field implementation 680 of one or more of the candidate demulsifiers 608, for example, as selected, ranked, etc., via at least one of the one or more models 650. As shown in FIG. 6, a workflow may aim to receive one type of data (e.g., as a digitized image, raw data, etc.) for a candidate demulsifier and output another type of data (e.g., as a digitized image, raw data, etc.) where the output characterizes performance of the candidate demulsifier (e.g., consider demulsifier efficiency).

As an example, the candidate demulsifiers 608 can include associated data such as, for example, metadata. For example, consider metadata that can be related to the field data 630, which can include specifications as to one or more field parameters (e.g., type of reservoir, type of fluid, type of equipment, residence times, etc.).

As an example, the one or more models 650 can leverage data from the one or more databases 640 for training (e.g., machine learning) such that a variety of inputs can be received regarding the candidate demulsifiers 608 to generate output as to predicted effectiveness of the candidate demulsifiers 608 without having to perform bottle testing on a number of the top ranked candidate demulsifiers 608. Or, for example, demand for bottle testing may be greatly diminished by narrowing a list of candidate demulsifiers to a few top ranked candidate demulsifiers.

As mentioned, a method can include simulation. For example, consider the output 670 including predicted time performance for a demulsifier that can be utilized to construct a water separation versus time curve. In such an example, a simulation can be performed, for example, for a separation process, where an amount of a selected demulsifier is injected that behaves according to the water separation versus time curve. Results from such a simulation may help to tailor an injection schedule, rate of injection, etc., with respect to one or more field parameters (e.g., flow rate, residence time, desired separation performance, etc.). Thus, the output 670 can include outputting information for one or more performance curves for one or more of the candidate demulsifiers 608. As an example, the output 670 may present information in a format akin to that of bottle test data and/or akin to that of field data, which can include performance versus time, concentration with respect to performance, concentration-based performance versus time, etc.

As an example, data in one or more databases can include relationships, which can be understood, uncovered, etc., using one or more techniques. For example, consider regression, correlation, etc. As an example, data may be organized as to tensiometer measurement parameters. For example, consider a generation of two-dimensional plots of bottle test dynamics versus viscoelastic properties and/or IFT. While such two-dimensional plots may be visually reviewed to understand some relationships, the combination of such plots or dimensions may involve more complex relationships.

As an example, relationships may be linear and/or nonlinear. As an example, a neural network model and a linear regression model may be implemented for linear relationships, noting that a linear regression can be computationally less demanding than a neural network model (e.g., as to training). However, for nonlinear relationships, a model can include, for example, a polynomial regression model, a support vector machine (SVM), random forests, etc., or, for example, a neural network model. Depending on the amount of data, a relatively modest sized neural network model may be computationally more efficient.

As an example, data may be represented visually such that a problem can be cast as an image-based problem. For example, consider images based on combinations of bottle test data and tensiometer data where a trained neural network can receive tensiometer data and predict what its bottle test data would look like in an image. Such a problem can be akin to filling in a missing portion of an image (e.g., bottle test data) when given part of the image (e.g., the tensiometer data). In such an approach, the missing portion may be synthetic, which may be performed via a generation process and/or actual, which may be performed via a matching process from information in a database. As to image-based approaches, a model can include a convolutional neural network (CNN). As an example, if a problem is cast as a time series problem, it may be handled using one or more recurrent neural networks and LSTMs (Long Short Term Memory). For example, as mentioned, performance of a demulsifier can be characterized using time series data such as, for example, separated water versus time, which may be available from bottle tests, field tests, etc. As an example, a framework can receive tensiometer data and relate that to separated water versus time data, which may be output in a manner that provides for ranking candidate demulsifiers.

As to regression and classification, these may be handled as separate tasks or combined tasks. Various techniques can be implemented to transform a regression type of problem into a classification type of problem and vice versa. As an example, efficiency of a candidate demulsifier may be predicted or efficiency of a candidate demulsifier may be in a class that can be determined by classification.

As explained, a framework may implement clustering or grouping, which can be a problem of recognition of similarities. As an example, a combined regression (prediction) and classification ML model may be constructed. For example, consider an architecture with an input layer, hidden layers and multiple output layers. In such an example, regression and classification output layers can be connected to a common last hidden layer of the model. Given two output layers, a model may be trained using two loss functions, for example, consider a mean squared error (MSE) loss for the regression output layer and a sparse categorical cross-entropy for the classification output layer. An example of a combined ML model for regression (prediction) and classification can be for determining the age of an abalone (e.g., a type of fish) from physical details, where predicting the number of rings of the abalone is a proxy for the age of the abalone (e.g., age can be predicted as both a numerical value (in years) or a class label (ordinal year as a class)). In various examples, a trained ML model may output probability information. For example, consider a probability that input belongs to a particular class.

As to types of machine learning models that may be utilized by a system, consider one or more of a support vector machine (SVM) model, a k-nearest neighbors (KNN) model, an ensemble classifier model, a neural network (NN) model, etc. As an example, a machine learning model can be a deep learning model (e.g., deep Boltzmann machine, deep belief network, convolutional neural network, stacked autoencoder, etc.), an ensemble model (e.g., random forest, gradient boosting machine, bootstrapped aggregation, AdaBoost, stacked generalization, gradient boosted regression tree, etc.), a neural network model (e.g., radial basis function network, perceptron, back-propagation, Hopfield network, etc.), a regularization model (e.g., ridge regression, least absolute shrinkage and selection operator, elastic net, least angle regression), a rule system model (e.g., cubist, one rule, zero rule, repeated incremental pruning to produce error reduction), a regression model (e.g., linear regression, ordinary least squares regression, stepwise regression, multivariate adaptive regression splines, locally estimated scatterplot smoothing, logistic regression, etc.), a Bayesian model (e.g., naïve Bayes, average on-dependence estimators, Bayesian belief network, Gaussian naïve Bayes, multinomial naïve Bayes, Bayesian network), a decision tree model (e.g., classification and regression tree, iterative dichotomiser 3, C4.5, C5.0, chi-squared automatic interaction detection, decision stump, conditional decision tree, M5), a dimensionality reduction model (e.g., principal component analysis, partial least squares regression, Sammon mapping, multidimensional scaling, projection pursuit, principal component regression, partial least squares discriminant analysis, mixture discriminant analysis, quadratic discriminant analysis, regularized discriminant analysis, flexible discriminant analysis, linear discriminant analysis, etc.), an instance model (e.g., k-nearest neighbor, learning vector quantization, self-organizing map, locally weighted learning, etc.), a clustering model (e.g., k-means, k-medians, expectation maximization, hierarchical clustering, etc.), etc.

As an example, the TENSORFLOW framework (Google LLC, Mountain View, California) may be implemented, which is an open-source software library for dataflow programming that includes a symbolic math library, which can be implemented for machine learning applications that can include neural networks. As an example, the CAFFE framework may be implemented, which is a DL framework developed by Berkeley AI Research (BAIR) (University of California, Berkeley, California). As another example, consider the SCIKIT platform (e.g., scikit-learn), which utilizes the PYTHON programming language. As an example, a framework such as the APOLLO AI framework may be utilized (APOLLO.AI GmbH, Germany). As mentioned, a framework such as the PYTORCH framework may be utilized.

As an example, a training method can include various actions that can operate on a dataset to train a ML model. As an example, a dataset can be split into training data and test data where test data can provide for evaluation. A method can include cross-validation of parameters and best parameters, which can be provided for model training.

The TENSORFLOW framework can run on multiple CPUs and GPUs (with optional CUDA (NVIDIA Corp., Santa Clara, California) and SYCL (The Khronos Group Inc., Beaverton, Oregon) extensions for general-purpose computing on graphics processing units (GPUs)). TENSOR-FLOW is available on 64-bit LINUX, MACOS (Apple Inc., Cupertino, California), WINDOWS (Microsoft Corp., Redmond, Washington), and mobile computing platforms including ANDROID (Google LLC, Mountain View, California) and IOS (Apple Inc.) operating system based platforms.

TENSORFLOW computations can be expressed as stateful dataflow graphs; noting that the name TENSORFLOW derives from the operations that such neural networks perform on multidimensional data arrays. Such arrays can be referred to as "tensors".

As an example, a device may utilize TENSORFLOW LITE (TFL) or another type of lightweight framework. TFL is a set of tools that enables on-device machine learning where models may run on mobile, embedded, and IoT devices. TFL is optimized for on-device machine learning, by addressing latency (no round-trip to a server), privacy (no personal data leaves the device), connectivity (Internet connectivity is demanded), size (reduced model and binary size) and power consumption (e.g., efficient inference and a lack of network connections). TFL includes multiple platform support, covering ANDROID and iOS devices, embedded LINUX, and microcontrollers along with diverse language support, which includes JAVA, SWIFT, Objective-C, C++, and PYTHON. TFL can provide high performance, with hardware acceleration and model optimization. Machine learning tasks that may be performed using TFL may include, for example, simulation, regression, classification, object detection, pose estimation, question answering, text classification, etc. As an example, a gateway may be installed at a site and provide for execution of a framework such as, for example, the TFL framework. In such an example, the gateway may provide for determining one or more control actions and issuance of one or more control actions at the site.

Figure 7:
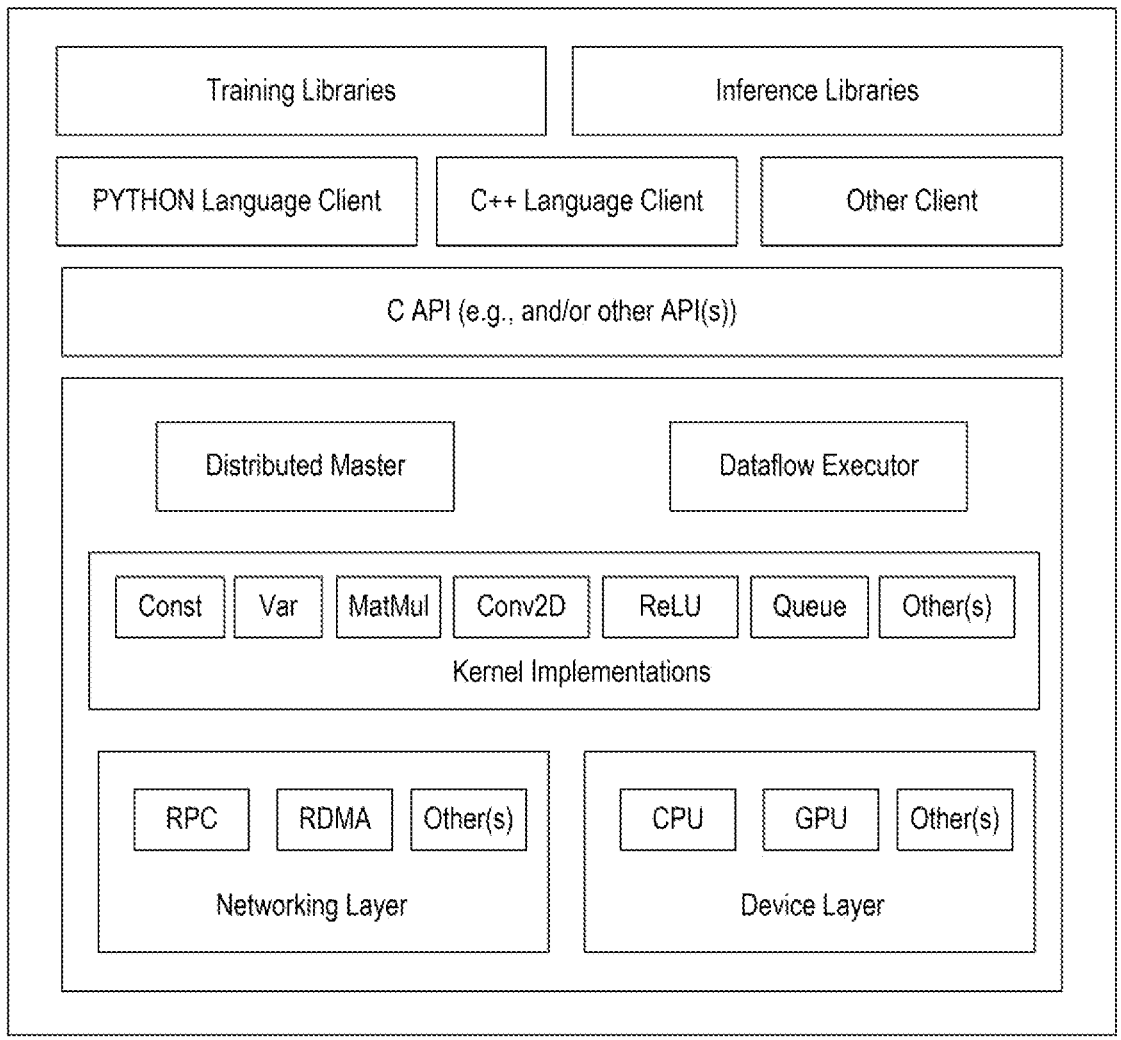
FIG. 7 is a diagram of an example of a framework.
Figure 7:
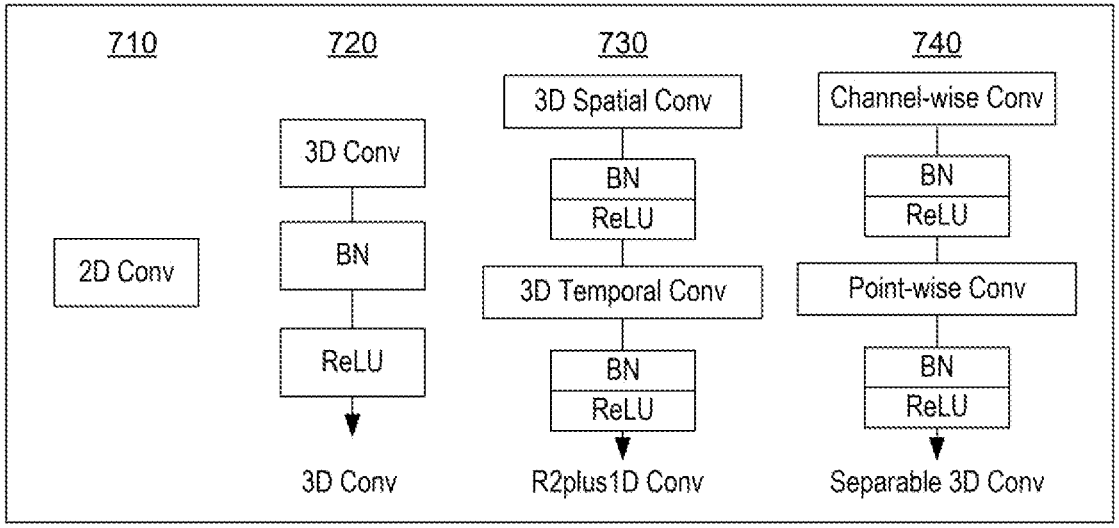

FIG. 7 shows an architecture 700 of a framework such as the TENSORFLOW framework. As shown, the architecture 700 includes various features. As an example, in the terminology of the architecture 700, a client can define a computation as a dataflow graph and, for example, can initiate graph execution using a session. As an example, a distributed master can prune a specific subgraph from the graph, as defined by the arguments to "Session.run( )"; partition the subgraph into multiple pieces that run in different processes and devices; distributes the graph pieces to worker services; and initiate graph piece execution by worker services. As to worker services (e.g., one per task), as an example, they may schedule the execution of graph operations using kernel implementations appropriate to hardware available (CPUs, GPUs, etc.) and, for example, send and receive operation results to and from other worker services. As to kernel implementations, these may, for example, perform computations for individual graph operations.

FIG. 7 also shows some examples of types of machine learning models 710, 720, 730, and 740, one or more of which may be utilized. As explained, a ML model-based approach can include receiving data that can be spatial and/or temporal data in multiple dimensions. As an example, time can be a dimension such that data can be spatial and temporal. As explained, frequency can be a dimension. As an example, a convolution neural network and/or one or more other types of neural networks can be utilized for spatial and/or spatial-temporal analysis.

Figure 8:
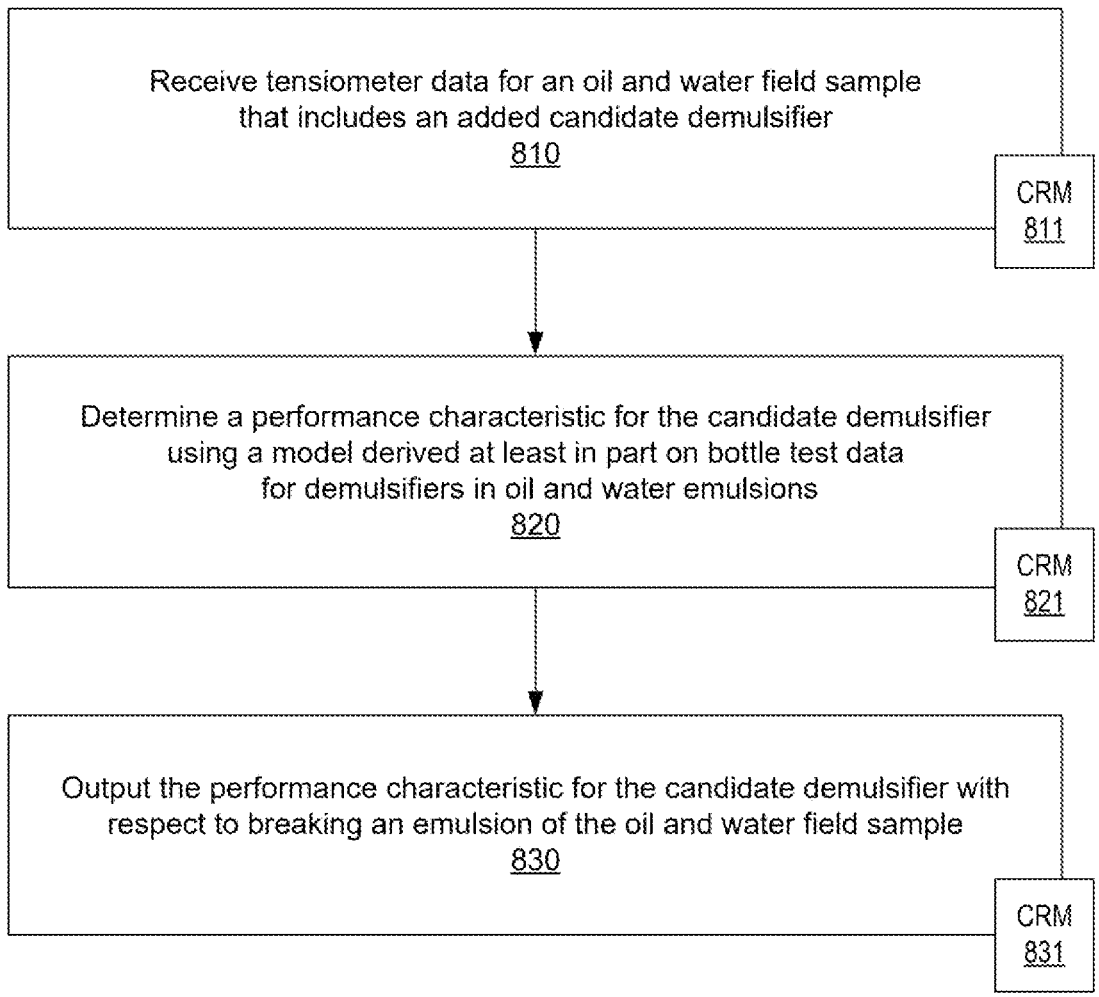
FIG. 8 is a diagram of an example of a method and an example of a system.
Figure 8:
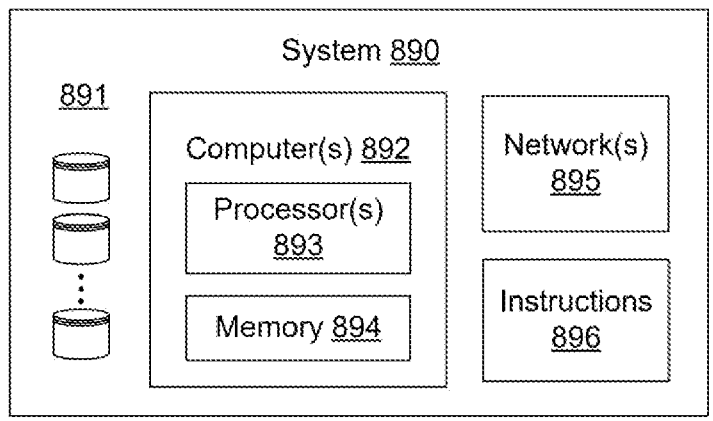

FIG. 8 shows an example of a method 800 and an example of a system 890. As shown, the method 800 includes a reception block 810 for receiving, by a demulsifier analysis framework, tensiometer data for an oil and water field sample that includes an added candidate demulsifier, where the tensiometer data include rheology data with respect to frequency and where the demulsifier analysis framework includes a model derived at least in part on bottle test data for demulsifiers in oil and water emulsions; a determination block 820 for determining a performance characteristic for the candidate demulsifier with respect to the oil and water field sample using the tensiometer data as input to the model of the demulsifier analysis framework without performing a bottle test on the oil and water field sample; and an output block 830 for outputting, by the demulsifier analysis framework, the performance characteristic for the candidate demulsifier with respect to breaking an emulsion of the oil and water field sample.

The method 800 is shown as including various computer-readable storage medium (CRM) blocks 811, 821, and 831 that can include processor-executable instructions that can instruct a computing system, which can be a control system, to perform one or more of the actions described with respect to the method 800.

In the example of FIG. 8, the system 890 includes one or more information storage devices 891, one or more computers 892, one or more networks 895 and instructions 896. As to the one or more computers 892, each computer may include one or more processors (e.g., or processing cores) 893 and a memory 894 for storing the instructions 896, for example, executable by at least one of the one or more processors 893 (see, e.g., the blocks 811, 821 and 831). As an example, a computer may include one or more network interfaces (e.g., wired or wireless), one or more graphics cards, a display interface (e.g., wired or wireless), etc.

As an example, the method 800 may be a workflow that can be implemented using one or more frameworks that may be within a framework environment. As an example, the system 890 can include local and/or remote resources. For example, consider a browser application executing on a client device as being a local resource with respect to a user of the browser application and a cloud-based computing device as being a remote resource with respect to the user. In such an example, the user may interact with the client device via the browser application where information is transmitted to the cloud-based computing device (or devices) and where information may be received in response and rendered to a display operatively coupled to the client device (e.g., via services, APIs, etc.).

As an example, a method can include receiving, by a demulsifier analysis framework, tensiometer data for an oil and water field sample that includes an added candidate demulsifier, where the tensiometer data include rheology data with respect to frequency and where the demulsifier analysis framework includes a model derived at least in part on bottle test data for demulsifiers in oil and water emulsions; determining a performance characteristic for the candidate demulsifier with respect to the oil and water field sample using the tensiometer data as input to the model of the demulsifier analysis framework without performing a bottle test on the oil and water field sample; and outputting, by the demulsifier analysis framework, the performance characteristic for the candidate demulsifier with respect to breaking an emulsion of the oil and water field sample. In such an example, the oil and water field sample can include crude oil and brine.

As an example, a method can include determining an amount of a candidate demulsifier to inject into well fluid of a field process, which may be, for example, a field process that includes an oil and water separation process.

As an example, an oil and water field sample can include an emulsion where, for example, a performance characteristic indicates an efficiency of the candidate demulsifier in breaking the emulsion.

As an example, a performance characteristic can be a demulsifier efficiency where, for example, the demulsifier efficiency is defined as a volume of separated water divided by an initial volume of water in an emulsion of the oil and water field sample.

As an example, a performance characteristic of a candidate demulsifier can be a rate where, for example, the rate includes a concentration dependent rate of the candidate demulsifier for separation of water from an emulsion of an oil and water field sample with respect to time.

As an example, a method can include performing a process separation simulation using a performance characteristic of a candidate demulsifier where, for example, the process separation simulation simulates fluid behavior in the presence of the candidate demulsifier for a separator in a field from which an oil and water field sample is collected.

As an example, rheology data can include one or more moduli, where the one or more moduli include one or more of a viscoelastic modulus, an elastic modulus and a viscous modulus.

As an example, a model can include a pixel image-based model.

As an example, a model can include one or more of a regression model and a classification model.

As an example, a model can relate received tensiometer data to at least a portion of previously acquired bottle test data (e.g., as may be present in a database).

As an example, a demulsifier analysis framework can include a tensiometer that generates tensiometer data.

As an example, a method can include determining a performance characteristic for a candidate demulsifier with respect to an oil and water field sample, without performance of a bottle test for the oil and water field sample, using tensiometer data as input to a model derived at least in part on bottle test data for demulsifiers in oil and water emulsions in a manner that occurs responsive to receipt of the tensiometer data. For example, laboratory equipment can include a tensiometer where a framework is operatively coupled to the tensiometer to receive tensiometer data therefrom and automatically generate output based on at least a portion of the tensiometer data using a model.

As an example, a system can include a processor; memory operatively coupled to the processor; and processor-executable instructions stored in the memory to instruct the system to: receive tensiometer data for an oil and water field sample that includes an added candidate demulsifier, where the tensiometer data include rheology data with respect to frequency; determine a performance characteristic for the candidate demulsifier with respect to the oil and water field sample, without performance of a bottle test for the oil and water field sample, using the tensiometer data as input to a model derived at least in part on bottle test data for demulsifiers in oil and water emulsions; and output the performance characteristic for the candidate demulsifier with respect to the oil and water field sample.

As an example, one or more computer-readable storage media can include processor-executable instructions to instruct a computing system to: receive tensiometer data for an oil and water field sample that includes an added candidate demulsifier, where the tensiometer data include rheology data with respect to frequency; determine a performance characteristic for the candidate demulsifier with respect to the oil and water field sample, without performance of a bottle test for the oil and water field sample, using the tensiometer data as input to a model derived at least in part on bottle test data for demulsifiers in oil and water emulsions; and output the performance characteristic for the candidate demulsifier with respect to the oil and water field sample.

A computer-readable storage medium (or computer-readable storage media) is non-transitory, not a signal and not a carrier wave. Rather, a computer-readable storage medium is a physical device that can be considered to be circuitry or hardware.

Figure 9:
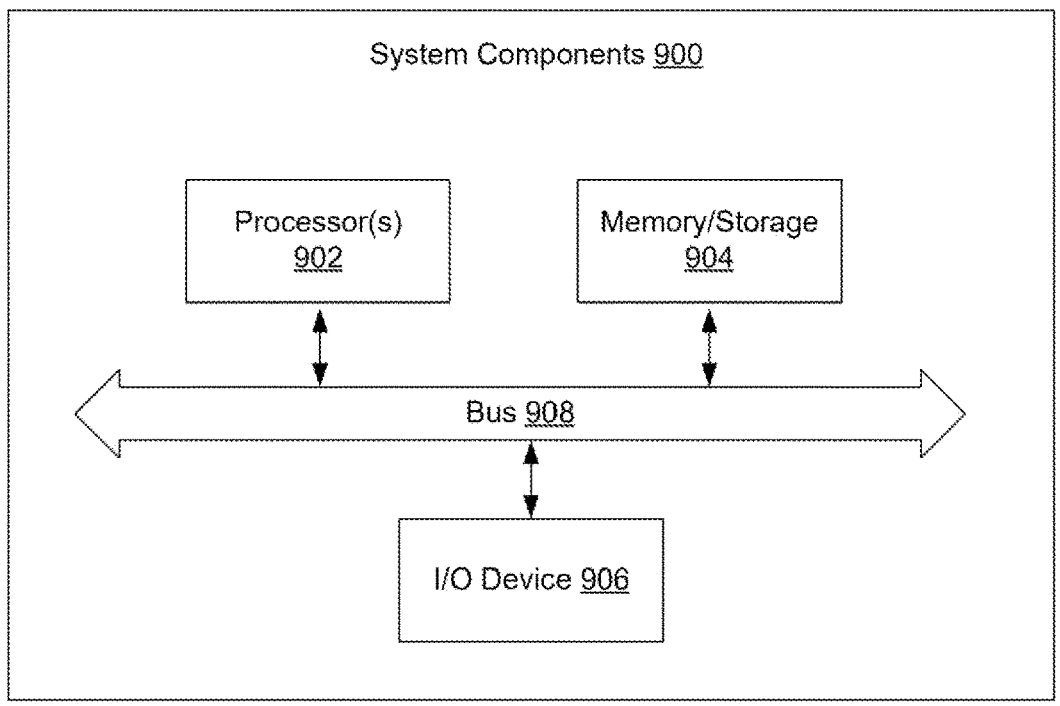
FIG. 9 illustrates example components of a system and a networked system.
Figure 9:
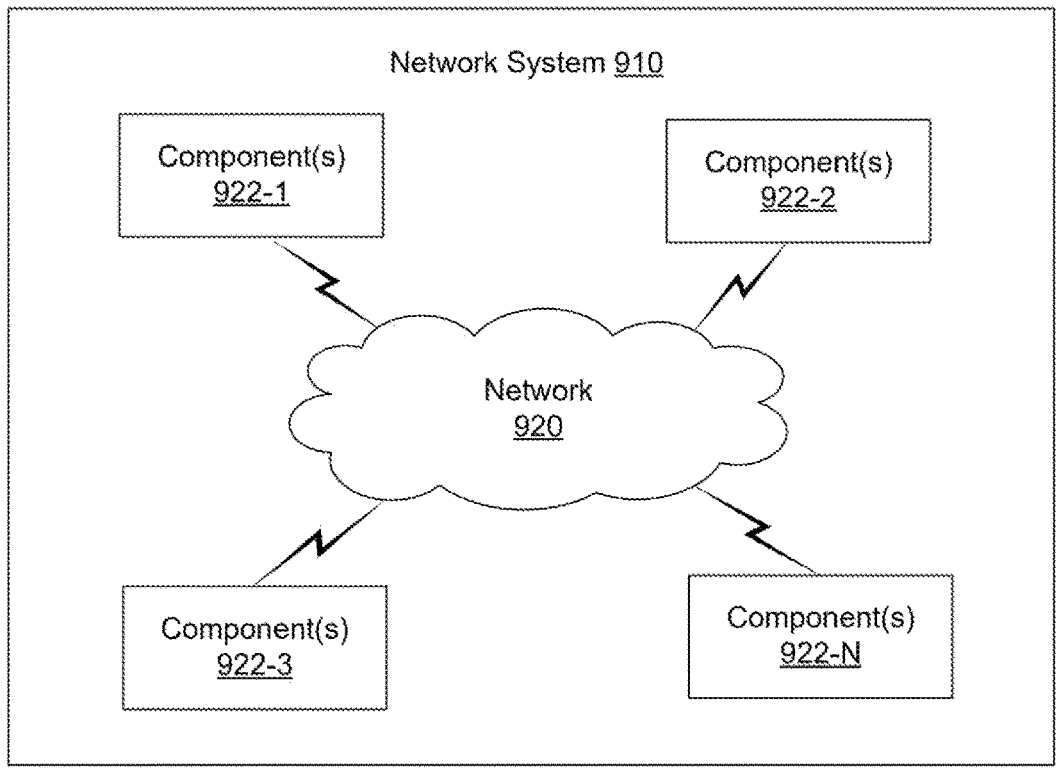

FIG. 9 shows components of an example of a computing system 900 and an example of a networked system 910 with a network 920. As an example, a demulsifier analysis framework may be implemented within the computing system 900, within the networked system 910, etc. The system 900 includes one or more processors 902, memory and/or storage components 904, one or more input and/or output devices 906 and a bus 908. In an example embodiment, instructions may be stored in one or more computer-readable media (e.g., memory/storage components 904). Such instructions may be read by one or more processors (e.g., the processor(s) 902) via a communication bus (e.g., the bus 908), which may be wired or wireless. The one or more processors may execute such instructions to implement (wholly or in part) one or more attributes (e.g., as part of a method). A user may view output from and interact with a process via an I/O device (e.g., the device 906). In an example embodiment, a computer-readable medium may be a storage component such as a physical memory storage device, for example, a chip, a chip on a package, a memory card, etc. (e.g., a computer-readable storage medium).

In an example embodiment, components may be distributed, such as in the network system 910. The network system 910 includes components 922-1, 922-2, 922-3, . . . 922-N. For example, the components 922-1 may include the processor(s) 902 while the component(s) 922-3 may include memory accessible by the processor(s) 902. Further, the component(s) 922-2 may include an I/O device for display and optionally interaction with a method. The network may be or include the Internet, an intranet, a cellular network, a satellite network, etc.

As an example, a device may be a mobile device that includes one or more network interfaces for communication of information. For example, a mobile device may include a wireless network interface (e.g., operable via IEEE 802.11, ETSI GSM, BLUETOOTH, satellite, etc.). As an example, a mobile device may include components such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

As an example, a system may be a distributed environment, for example, a so-called "cloud" environment where various devices, components, etc. interact for purposes of data storage, communications, computing, etc. As an example, a device or a system may include one or more components for communication of information via one or more of the Internet (e.g., where communication occurs via one or more Internet protocols), a cellular network, a satellite network, etc. As an example, a method may be implemented in a distributed environment (e.g., wholly or in part as a cloud-based service).

As an example, information may be input from a display (e.g., consider a touchscreen), output to a display or both. As an example, information may be output to a projector, a laser device, a printer, etc. such that the information may be viewed. As an example, information may be output stereographically or holographically. As to a printer, consider a 2D or a 3D printer. As an example, a 3D printer may include one or more substances that can be output to construct a 3D object. For example, data may be provided to a 3D printer to construct a 3D representation of a subterranean formation. As an example, layers may be constructed in 3D (e.g., horizons, etc.), geobodies constructed in 3D, etc. As an example, holes, fractures, etc., may be constructed in 3D (e.g., as positive structures, as negative structures, etc.).

Although only a few example embodiments have been described in detail above, those skilled in the art will readily appreciate that many modifications are possible in the example embodiments. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A method comprising:
    measuring, via a tensiometer, an oil and water field sample that comprises an added candidate demulsifier;
    generating tensiometer data via the tensiometer based on the measuring of the oil and water field sample that comprises the added candidate demulsifier;
    transmitting the tensiometer data from the tensiometer to a demulsifier analysis framework;
    receiving, by the demulsifier analysis framework, the tensiometer data for the oil and water field sample that comprises the added candidate demulsifier, wherein the tensiometer data comprise rheology data with respect to frequency and wherein the demulsifier analysis framework comprises a model derived at least in part on bottle test data for demulsifiers in oil and water emulsions;
    determining a performance characteristic for the added candidate demulsifier with respect to the oil and water field sample using the tensiometer data as input to the model of the demulsifier analysis framework without performing a bottle test on the oil and water field sample; and
    outputting, by the demulsifier analysis framework, the performance characteristic for the added candidate demulsifier with respect to breaking an emulsion of the oil and water field sample.

2. The method of claim 1, wherein the oil and water field sample comprises crude oil and brine.

3. The method of claim 1, comprising determining an amount of the added candidate demulsifier to inject into well fluid of a field process.

4. The method of claim 3, wherein the field process comprises an oil and water separation process.

5. The method of claim 1, wherein the oil and water field sample comprises an emulsion.

6. The method of claim 5, wherein the performance characteristic indicates an efficiency of the added candidate demulsifier in breaking the emulsion.

7. The method of claim 1, wherein the performance characteristic comprises a demulsifier efficiency.

8. The method of claim 7, wherein the demulsifier efficiency is defined as a volume of separated water divided by an initial volume of water in an emulsion of the oil and water field sample.

9. The method of claim 1, wherein the performance characteristic of the added candidate demulsifier comprises a rate, wherein the rate comprises a concentration dependent rate of the added candidate demulsifier for separation of water from an emulsion of the oil and water field sample with respect to time.

10. The method of claim 1, comprising performing a process separation simulation using the performance characteristic of the added candidate demulsifier.

11. The method of claim 10, wherein the process separation simulation simulates fluid behavior in the presence of the added candidate demulsifier for a separator in a field from which the oil and water field sample is collected.

12. The method of claim 1, wherein the rheology data comprise one or more moduli, wherein the one or more moduli comprise one or more of a viscoelastic modulus, an elastic modulus and a viscous modulus.

13. The method of claim 1, wherein the model comprises a pixel image-based model.

14. The method of claim 1, wherein the model comprises one or more of a regression model and a classification model.

15. The method of claim 1, wherein the model relates the received tensiometer data to at least a portion of the bottle test data.

16. A system comprising:
    a tensiometer, configured to:
        measure an oil and water field sample that comprises an added candidate demulsifier;
        generate tensiometer data based on measuring of the oil and water field sample that comprises the added candidate demulsifier; and
        transmit the tensiometer data from the tensiometer to a demulsifier analysis framework;
    a processor;
    memory operatively coupled to the processor; and
    processor-executable instructions stored in the memory to instruct the system to:
        receive the tensiometer data for the oil and water field sample that comprises the added candidate demulsifier, wherein the tensiometer data comprise rheology data with respect to frequency;
        determine a performance characteristic for the added candidate demulsifier with respect to the oil and water field sample, without performance of a bottle test for the oil and water field sample, using the tensiometer data as input to a model derived at least in part on bottle test data for demulsifiers in oil and water emulsions; and output the performance characteristic for the added candidate demulsifier with respect to the oil and water field sample.

17. One or more computer-readable storage media comprising processor-executable instructions to instruct a computing system to:

receive tensiometer data for an oil and water field sample that comprises an added candidate demulsifier from a tensiometer configured to measure the oil and water field sample that comprises the added candidate demulsifier and generate the tensiometer data based on measuring of the oil and water field sample that comprises the added candidate demulsifier, wherein the tensiometer data comprise rheology data with respect to frequency;

determine a performance characteristic for the added candidate demulsifier with respect to the oil and water field sample, without performance of a bottle test for the oil and water field sample, using the tensiometer data as input to a model derived at least in part on bottle test data for demulsifiers in oil and water emulsions; and output the performance characteristic for the added candidate demulsifier with respect to the oil and water field sample.

* * * * *